(12) United States Patent
Freeman et al.

(10) Patent No.: US 12,251,199 B2
(45) Date of Patent: Mar. 18, 2025

(54) SYSTEMS AND METHODS FOR TESTING A MEDICAL DEVICE

(71) Applicant: ZOLL Medical Corporation, Chelmsford, MA (US)

(72) Inventors: Gary A. Freeman, Waltham, MA (US); Shane S. Volpe, Saltsburg, PA (US); Timothy F. Stever, Lowell, MA (US); Thomas E. Kaib, Irwin, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 18/322,322

(22) Filed: May 23, 2023

(65) Prior Publication Data

US 2023/0293022 A1  Sep. 21, 2023

Related U.S. Application Data

(63) Continuation of application No. 17/455,955, filed on Nov. 22, 2021, now Pat. No. 11,701,006, which is a
(Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1117* (2013.01); *A61B 5/6805* (2013.01);
(Continued)

(58) Field of Classification Search
None
See application file for complete search history.

(56) References Cited

U.S. PATENT DOCUMENTS 3,922,665 A   11/1975  Curry et al.
4,576,170 A    3/1986  Bradley et al.
(Continued)

FOREIGN PATENT DOCUMENTS

EP   0707825 A2   4/1996
EP   0761255 A1   3/1997
(Continued)

OTHER PUBLICATIONS

"ATS statement: Guidelines for the Six-Minute Walk Test", American Journal of Respiratory and Critical Care Medicine, vol. 166, pp. 111-117 (2002), American Thoracic Society, <URL: http;/ajrccm.atsjournals.org/cgi/content/ull/166/1/111>.
(Continued)

*Primary Examiner* — Farhana A Hoque
(74) *Attorney, Agent, or Firm* — Finch & Maloney PLLC

(57) ABSTRACT

An ambulatory medical device comprises: a sensing component to be disposed on a patient for detecting a physiological signal of the patient; and monitoring and self-test circuitry configured for detecting a triggering event and initiating one or more self-tests based on detection of the triggering event. The ambulatory medical device senses the physiological signal of the patient substantially continuously over an extended period of time.

21 Claims, 11 Drawing Sheets

Related U.S. Application Data continuation of application No. 16/926,168, filed on Jul. 10, 2020, now Pat. No. 11,213,211, which is a continuation of application No. 16/299,277, filed on Mar. 12, 2019, now Pat. No. 10,744,057, which is a continuation of application No. 15/073,923, filed on Mar. 18, 2016, now Pat. No. 10,272,010.

(60) Provisional application No. 62/135,910, filed on Mar. 20, 2015.

(51) Int. Cl.
  *A61B 5/11* (2006.01)
  *A61B 5/333* (2021.01)
  *A61H 3/00* (2006.01)
  *A61N 1/39* (2006.01)

(52) U.S. Cl.
  CPC .......... *A61B 5/7282* (2013.01); *A61B 5/7285* (2013.01); *A61H 3/00* (2013.01); *A61N 1/39* (2013.01); *A61N 1/3904* (2017.08); *A61N 1/3925* (2013.01); *A61B 5/333* (2021.01); *A61B 2560/0242* (2013.01); *A61B 2560/0266* (2013.01); *A61B 2560/0276* (2013.01); *A61N 1/3993* (2013.01)

(56) References Cited

U.S. PATENT DOCUMENTS

| | | |
|---|---|---|
| 4,580,572 A | 4/1986 | Granek et al. |
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,348,008 A | 9/1994 | Bornn et al. |
| 5,371,692 A | 12/1994 | Draeger et al. |
| 5,381,798 A | 1/1995 | Burrows |
| 5,645,571 A | 7/1997 | Olson et al. |
| 5,741,306 A | 4/1998 | Glegyak et al. |
| 5,749,913 A | 5/1998 | Cole |
| 5,879,374 A | 3/1999 | Powers et al. |
| 5,899,925 A | 5/1999 | Ochs et al. |
| 5,919,212 A | 7/1999 | Olson et al. |
| 5,929,601 A | 7/1999 | Kaib et al. |
| 5,944,669 A | 8/1999 | Kaib |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,304,780 B1 | 10/2001 | Owen et al. |
| 6,336,900 B1 | 1/2002 | Alleckson et al. |
| 6,374,138 B1 | 4/2002 | Owen et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,668,192 B1 | 12/2003 | Parker et al. |
| 6,681,003 B2 | 1/2004 | Linder et al. |
| 6,694,191 B2 | 2/2004 | Starkweather et al. |
| 6,804,554 B2 | 10/2004 | Ujhelyi et al. |
| 6,865,413 B2 | 3/2005 | Halperin et al. |
| 6,889,078 B2 | 5/2005 | Struble et al. |
| 6,889,079 B2 | 5/2005 | Bocek et al. |
| 6,908,437 B2 | 6/2005 | Bardy |
| 7,088,233 B2 | 8/2006 | Menard |
| 7,108,665 B2 | 9/2006 | Halperin et al. |
| 7,149,579 B1 | 12/2006 | Koh et al. |
| 7,220,235 B2 | 5/2007 | Geheb et al. |
| 7,295,871 B2 | 11/2007 | Halperin et al. |
| 7,340,296 B2 | 3/2008 | Stahmann et al. |
| 7,353,063 B2 | 4/2008 | Simms, Jr. |
| 7,439,705 B2 | 10/2008 | Koike |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,627,372 B2 | 12/2009 | Vaisnys et al. |
| 7,712,373 B2 | 5/2010 | Nagle et al. |
| 7,827,005 B2 | 11/2010 | Kimball |
| 7,831,303 B2 | 11/2010 | Rueter et al. |
| 7,913,015 B2 | 3/2011 | Kallmyer et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,005,552 B2 | 8/2011 | Covey et al. |
| 8,121,683 B2 | 2/2012 | Bucher et al. |
| 8,140,154 B2 | 3/2012 | Donnelly et al. |
| 8,224,441 B2 | 7/2012 | Vaisnys et al. |
| 8,234,128 B2 | 7/2012 | Martucci et al. |
| 8,271,082 B2 | 9/2012 | Donnelly et al. |
| 8,319,632 B1 | 11/2012 | Vaisnys et al. |
| 8,334,768 B2 | 12/2012 | Eaton et al. |
| 8,369,944 B2 | 2/2013 | Macho et al. |
| 8,406,842 B2 | 3/2013 | Kaib et al. |
| 8,475,367 B1 | 7/2013 | Yuen et al. |
| 8,494,628 B2 | 7/2013 | Vaisnys et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,768,441 B2 | 7/2014 | De Zwart et al. |
| 8,774,917 B2 | 7/2014 | Macho et al. |
| 8,781,577 B2 | 7/2014 | Freeman |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly et al. |
| 10,029,108 B2 | 7/2018 | Powers et al. |
| 10,426,342 B2 | 10/2019 | Patrick et al. |
| 10,561,852 B2 | 2/2020 | Murphy et al. |
| 11,202,569 B2 | 12/2021 | Patrick et al. |
| 2001/0031991 A1 | 10/2001 | Russial |
| 2002/0052539 A1 | 5/2002 | Haller et al. |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0212311 A1 | 11/2003 | Nova et al. |
| 2004/0049233 A1 | 3/2004 | Edwards |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0015148 A1 | 1/2006 | Mccabe et al. |
| 2006/0059976 A1 | 3/2006 | Simonenko et al. |
| 2006/0095091 A1 | 5/2006 | Drew |
| 2006/0136000 A1 | 6/2006 | Bowers |
| 2006/0211934 A1 | 9/2006 | Hassonjee et al. |
| 2006/0259080 A1 | 11/2006 | Vaisnys et al. |
| 2007/0129769 A1 | 6/2007 | Bourget et al. |
| 2007/0232946 A1 | 10/2007 | Feild et al. |
| 2008/0001735 A1 | 1/2008 | Tran |
| 2008/0033495 A1 | 2/2008 | Kumar |
| 2008/0058884 A1 | 3/2008 | Matos |
| 2008/0097791 A1 | 4/2008 | Alsafadi |
| 2008/0097793 A1 | 4/2008 | Dicks et al. |
| 2008/0103402 A1 | 5/2008 | Stickney et al. |
| 2008/0249591 A1 | 10/2008 | Gaw et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0058635 A1 | 3/2009 | Lalonde et al. |
| 2009/0073991 A1 | 3/2009 | Landrum et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076559 A1 | 3/2009 | Libbus et al. |

(56) References Cited

U.S. PATENT DOCUMENTS

| | | |
|---|---|---|
| 2009/0146822 A1 | 6/2009 | Soliman |
| 2009/0234410 A1 | 9/2009 | Libbus et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0010559 A1 | 1/2010 | Zhang et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0266251 A1 | 10/2012 | Birtwhistle et al. |
| 2012/0277642 A1 | 11/2012 | Smith et al. |
| 2012/0277645 A1 | 11/2012 | Kikuta et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0066653 A1 | 3/2013 | Joao et al. |
| 2013/0085538 A1 | 4/2013 | Volpe et al. |
| 2013/0113496 A1 | 5/2013 | Craige, III et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0004814 A1 | 1/2014 | Elghazzawi |
| 2014/0031884 A1 | 1/2014 | Elghazzawi |
| 2014/0031885 A1 | 1/2014 | Elghazzawi et al. |
| 2014/0046391 A1 | 2/2014 | Cowan et al. |
| 2014/0163334 A1 | 6/2014 | Volpe et al. |
| 2014/0206974 A1 | 7/2014 | Volpe et al. |
| 2014/0249613 A1 | 9/2014 | Kaib |
| 2014/0266718 A1 | 9/2014 | Bongberg et al. |
| 2014/0277243 A1 | 9/2014 | Maskara et al. |
| 2014/0288609 A1 | 9/2014 | Freeman |
| 2014/0288610 A1 | 9/2014 | Freeman |
| 2014/0303680 A1 | 10/2014 | Donnelly et al. |
| 2014/0324112 A1 | 10/2014 | Macho et al. |
| 2014/0336514 A1 | 11/2014 | Peyman |
| 2014/0379255 A1 | 12/2014 | Johnson |
| 2015/0005588 A1 | 1/2015 | Herken et al. |
| 2015/0035654 A1 | 2/2015 | Kaib et al. |
| 2015/0037636 A1 | 2/2015 | Amsler et al. |
| 2015/0039039 A1 | 2/2015 | Macho et al. |
| 2015/0039042 A1* | 2/2015 | Amsler ............... A61B 90/98 607/7 |
| 2015/0039053 A1 | 2/2015 | Kaib et al. |
| 2015/0080699 A1 | 3/2015 | Kaib et al. |
| 2015/0224330 A1 | 8/2015 | Kaib et al. |
| 2015/0321022 A1 | 11/2015 | Sullivan et al. |
| 2016/0015986 A1 | 1/2016 | Seeberger et al. |
| 2016/0274162 A1* | 9/2016 | Freeman ............... A61N 1/39 |
| 2017/0065823 A1 | 3/2017 | Kaib et al. |
| 2017/0199797 A1 | 7/2017 | Hresko et al. |

FOREIGN PATENT DOCUMENTS

| | | |
|---|---|---|
| JP | 11149379 A | 6/1999 |
| JP | 2002-509472 A | 3/2002 |
| JP | 2002-514107 A | 5/2002 |
| JP | 2004-318839 A | 11/2004 |
| JP | 2006-091013 A | 4/2006 |
| JP | 2008-302225 A | 12/2008 |
| JP | 2008-302228 A | 12/2008 |
| JP | 2009-510631 A | 3/2009 |
| JP | 2009-521865 A | 6/2009 |
| JP | 2009-528909 A | 8/2009 |
| JP | 2012-003311 A | 1/2012 |
| WO | 8304171 A1 | 12/1983 |
| WO | 1997022297 A1 | 6/1997 |
| WO | 1998039061 A2 | 9/1998 |
| WO | 2000030529 A1 | 6/2000 |
| WO | 2004078259 A1 | 9/2004 |
| WO | 2007019325 A2 | 2/2007 |
| WO | 2009034506 A1 | 3/2009 |
| WO | 2009122277 A2 | 10/2009 |
| WO | 2011027459 A1 | 3/2011 |
| WO | 2012006524 A1 | 1/2012 |
| WO | 2012100219 A1 | 7/2012 |
| WO | 2012149482 A2 | 11/2012 |
| WO | 2013040214 A1 | 3/2013 |
| WO | 2013130957 A2 | 9/2013 |
| WO | 2014018057 A1 | 1/2014 |
| WO | 2014018160 A1 | 1/2014 |
| WO | 2014097035 A1 | 6/2014 |
| WO | 2014099986 A1 | 6/2014 |

OTHER PUBLICATIONS

Association for the Advancement of Medical Instrumentation, ANSI/AAMI DF80:2003, "Medical Electrical Equipment—Part 2-4: Particular Requirements for the Safety of Cardiac Defibrillators (including Automated External Defibrillators)", 2004, ISBN1-57020-210-9; abstract; p. vi; p. 50, section 107.1.2.

http://web.archive.org/web/20030427001846/http:/www.lifecor.comiimagelib/imageproduct.asp; Published by LifeCor, Inc., 2002 on a web page owned by LifeCor Inc.

Zoll Medical Corporation, "LifeVest Model WCD 3000 Operator's Manual", Pittsburgh, PA.

PCT Search Report and Written Opinion for PCT Application No. PCT/US2016/023057 dated Sep. 6, 2016, 14 pages.

International Search Report and Written Opinion from PCT/US2013/028598 mailed May 9, 2013.

Fuertes et al., "Pacemaker Lead Displacement: Mechanisms and Management", Indian Pacing and Electrophysiology Journal, 3(4): 231238 (2003).

* cited by examiner

| NON-EXHAUSTIVE LIST OF EXEMPLARY TRIGGERING EVENTS FOR SELF-TESTS |
| --- |
| 1. INITIALIZATION AND BASELINING; |
| 2. DOWNLOAD OF PATIENT PROFILE; |
| 3. BUTTON(S) ACTUATION DETECTION; |
| 4. MECHANICAL IMPACT DETECTION; |
| 5. REMOTELY INITIATED SELF-TEST(S); |
| 6. EXECUTION-TIME DOWNLOAD SELF-TEST(S); |
| 7. ASSEMBLY/DIS-ASSEMBLY SENSING; |
| 8. ROUND ROBIN TESTING; |
| 9. SERIALIZED MISMATCH DETECTION; |
| 10. CURRENT SENSING; |
| 11. TEMPERATURE SENSING; |
| 12. MOISTURE SENSING; |
| 13. GAS GAUGE LEVEL SENSING; |
| 14. BATTERY VOLTAGE LEVEL DETECTION; |
| 15. CRITICAL ERROR HANDLING; |
| 16. BATTERY REPLACEMENT; |
| 17. ELECTRODE / THERAPY PAD PLACEMENT SENSING; |
| 18. COUNTDOWN TIMER; |
| 19. MULTI-TASKING; |
| 20. USER ACTIVITY; |
| 21. POST SHOCK DELIVERY; |
| 22. UPLOAD OR DOWNLOAD OF DATA; |
| 23. PRESSURE SENSING; |
| 24. AMBIENT PRESSURE; |
| 25. EXCESS STRAIN DETECTION; |
| 26. TAMPERING; |
| 27. ANY COMBINATION OF THE ABOVE. |

FIG. 8

| NON-EXHAUSTIVE LIST OF EXEMPLARY SELF-TESTS: |
|---|
| 1. BATTERY CAPACITY; |
| 2. REMAINING BATTERY RUN TIME; |
| 3. BATTERY STATUS; |
| 4. STATUS OF USER RESPONSE BUTTONS; |
| 5. DETERMINE IF ECG MONITORING SIGNAL QUALITY IS COMPRISED BY NOISE OR ELECTRODE FALL-OFF; |
| 6. ECG SIGNAL INTENSITY; |
| 7. CONFIRM DETECTION ALGORITHM PARAMETERS, THERAPY ELECTRODE PLACEMENT AND IMPEDANCE LEVELS; |
| 8. OPERATION OF VARIOUS ELECTRICAL COMPONENTS, SUBSYSTEMS, OR SYSTEMS, FOR EXAMPLE, A DC-DC CONVERTER OF THE DEFIBRILLATOR; |
| 9. BACKGROUND CHECKS OF INPUTS AND OUTPUTS (I/O); |
| 10. TESTS OF BATTERY VOLTAGE, CAPACITOR VOLTAGE, AND/OR DC-DC CONVERTER; |
| 11. SYSTEM-WIDE TESTS, SUCH AS TESTING BATTERY POWER CONSUMPTION, BATTERY VOLTAGE CHANGING FASTER/SLOWER THAN IT SHOWS, ONE OR MORE INDIVIDUAL COMPONENT CHECKS, LIKE INTERNAL RESISTANCE OF THE BATTERY, AND THE LIKE; |
| 12. LOOKING AT THE VALUES OF INDIVIDUAL PARTS; |
| 13. MICROPROCESSOR SELF-TEST; |
| 14. GATE ARRAY TEST; |
| 15. SYSTEM MONITOR TEST; |
| 16. CRC TEST; |
| 17. RAM/ROM TEST; |
| 18. WATCHDOG TIMER TEST; |
| 19. REMOVABLE MEMORY CARD TEST; |
| 20. ELECTRODE TEST; |
| 21. BATTERY TEST; |
| 22. BATTERY CHARGING TEST; |
| 23. POWER CONVERTER TEST; |
| 24. CAPACITOR CHARGE RETENTION TEST; |
| 25. CAPACITOR CHARGE/DISCHARGE TEST; |
| 26. PATIENT DISCHARGE RESISTOR TEST; |
| 27. SHOCK DISCHARGE TEST; |
| 28. THERAPY ELECTRODE PAD CELL / BLADDER INTEGRITY TEST; |
| 29. ELECTRODE / THERAPY PAD PLACEMENT TEST; |
| 30. USER INTERFACE TEST; |
| 31. ROUND ROBIN TESTING; |
| 32. ANY COMBINATION OF THE ABOVE. |

FIG. 9

SYSTEMS AND METHODS FOR TESTING A MEDICAL DEVICE

CROSS REFERENCE TO RELATED APPLICATIONS

This application is a continuation of U.S. patent application Ser. No. 17/455,955 (filed 22 Nov. 2021), which is a continuation of U.S. patent application Ser. No. 16/926,168 (filed 10 Jul. 2020, now U.S. Pat. No. 11,213,211), which is a continuation of U.S. patent application Ser. No. 16/299,277 (filed 12 Mar. 2019, now U.S. Pat. No. 10,744,057), which is a continuation of U.S. patent application Ser. No. 15/073,923 (filed 18 Mar. 2016, now U.S. Pat. No. 10,272,010), which claims the benefit of U.S. Provisional Patent Application 62/135,910 (filed 20 Mar. 2015), each of which is hereby incorporated herein by reference in its entirety.

BACKGROUND

Technical Field

The present disclosure relates to a wearable medical device and, in some aspects, to self-testing of a medical device.

Description of Related Art

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each can lead to death within minutes unless corrected by the appropriate electrical stimulation.

One of the most deadly forms of heart arrythmias is ventricular fibrillation, which occurs when the normal, regular electrical impulses am replaced by irregular and rapid impulses, causing the heart muscle to stop normal contractions and to begin to quiver. Normal blood flow ceases, and organ damage or death can result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment can result in death, implantable pacemakers and defibrillators have significantly improved the ability to treat these otherwise life-threatening conditions. Being implanted within the patient, the device continuously monitors the patient's heart for treatable arrhythmias and, when such is detected, the device applies corrective electrical pulses directly to the heart.

Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it cannot be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients that have recently had a heart attack or am awaiting such an implantable device, can be kept in a hospital where corrective electrical therapy is generally close at hand. Long-term hospitalization is frequently impractical due to its high cost, or due to the need for patients to engage in normal daily activities.

Wearable defibrillators have been developed for patients that have recently experienced a heart attack, that am susceptible to heart arrhythmias and are at temporary risk of sudden death, and that are awaiting an implantable device. While these wearable defibrillators have been widely accepted and have a good reputation in the marketplace, it remains desirable to develop improvements of such devices.

SUMMARY

Non-limiting examples of the embodiments will now be described in the following numbered clauses.

Clause 1: In an example, an ambulatory medical device comprises: a sensing component to be disposed on a patient for detecting a physiological signal of the patient; and monitoring and self-test circuitry configured for detecting a triggering event and initiating one or more self-tests based on detection of the triggering event, wherein the ambulatory medical device senses the physiological signal of the patient substantially continuously over an extended period of time.

Clause 2: The ambulatory medical device of clause 1, wherein the triggering event comprises at least one of an impact and a vibration event experienced by the ambulatory medical device.

Clause 3: The ambulatory medical device of clauses 1 or 2, wherein the at least one of the impact and the vibration event experienced by the ambulatory medical device corresponds to one of an impact level that exceeds a predetermined impact level and a vibration level that exceeds a predetermined vibration level.

Clause 4: The ambulatory medical device of any of clauses 1-3, wherein at least one of the impact and the vibration event experienced by the ambulatory medical device corresponds to an impact duration that exceeds a predetermined impact duration and a vibration duration that exceeds a predetermined vibration duration.

Clause 5: The ambulatory medical device of any of clauses 1-4, further comprising an electromechanical switch for detecting the at least one of the impact and the vibration event experienced by the ambulatory medical device.

Clause 6: The ambulatory medical device of any of clauses 1-5, further comprising at least one of a single axis accelerometer, a multi-axis accelerometer, and a piezoelectric transducer for detecting the at least one of the impact and the vibration event experienced by the ambulatory medical device.

Clause 7: The ambulatory medical device of any of clauses 1-6, wherein the one or more self-tests comprise tests of at least one of a device, component, and subsystem of the ambulatory medical device to ensure that the at least one of the impact and the vibration event has not adversely affected the at least one of the device, component, and subsystem.

Clause 8: The ambulatory medical device of any of clauses 1-7, wherein the triggering event comprises at least one of a software update, a device configuration update, and a patient parameter change.

Clause 9: The ambulatory medical device of clause 8, wherein the at least one of the software update, the device configuration update, and the patient parameter change is initiated remotely.

Clause 10: The ambulatory medical device of clauses 8 or 9, wherein the device configuration update comprises an update to one or more device parameters set in the ambulatory medical device.

Clause 11: The ambulatory medical device of any of clauses 1-10, wherein the triggering event is based on a user action or activity.

Clause 12: The ambulatory medical device of any of clauses 1-11, wherein the triggering event is a wireless test signal.

Clause 13: The ambulatory medical device of clause 12, wherein the wireless test signal is initiated at a remote support center.

Clause 14: The ambulatory medical device of any of clauses 1-13, wherein the triggering event is based on a detecting of at least one of battery replacement, battery removal, and battery ejection.

Clause 15: The ambulatory medical device of any of clauses 1-14, wherein the triggering event is based on a battery level transgressing a predetermined battery charge threshold.

Clause 16: The ambulatory medical device of any of clauses 1-15, wherein the triggering event is based on a signal indicating that one or more electrodes is making insufficient contact with the patient's skin.

Clause 17: The ambulatory medical device of any of clauses 1-16, wherein the triggering event is in response to detecting moisture in excess of a predetermined moisture level.

Clause 18: The ambulatory medical device of any of clauses 1-17, wherein the triggering event is in response to detecting strain on a device component in excess of a predetermined strain level.

Clause 19: The ambulatory medical device of any of clauses 1-18, wherein the triggering event is in response to detecting a temperature of at least one of the device or a component of the device greater than a predetermined maximum temperature or less than a predetermined minimum temperature.

Clause 20: The ambulatory medical device of any of clauses 1-19, wherein the triggering event is in response to detecting an operative connection between one or more electrodes and the medical device.

Clause 21: The ambulatory medical device of any of clauses 1-20, wherein the triggering event comprises at least one of replacement of a garment that comprises the ambulatory medical device worn about a torso of the patient, replacement of a patient signal sensor, and a prompt for replacement of at least one of the garment and the patient signal sensor in response to wear of the at least one of the garment and the patient signal sensor over time due to use.

Clause 22: The ambulatory medical device of any of clauses 1-21, wherein the one or more self-tests comprise one or more tests related to a type of the triggering event.

Clause 23: The ambulatory medical device of any of clauses 1-22, wherein the triggering event is initiated by or within a device, component, subsystem of the ambulatory medical device, and the one or more self-tests comprise one or more tests of the device, component, or subsystem of the ambulatory medical device that initiated or caused the triggering event.

Clause 24: The ambulatory medical device of any of clauses 1-23, wherein the monitoring and self-test circuitry is configured to classify the triggering event and, based on the classification, determine whether to initiate a self-test of the continuous-use medical device.

Clause 25: The ambulatory medical device of any of clauses 1-24, wherein the monitoring and self-test circuitry is configured to store a flag in a memory of the ambulatory medical device indicating a status of the triggering event.

Clause 26: The ambulatory medical device of any of clauses 1-25, wherein the monitoring and self-test circuitry is always operational for the monitoring whether a primary source of power is available in the ambulatory medical device.

Clause 27: The ambulatory medical device of clause 26, wherein the primary source of power is a main battery for use with the ambulatory medical device.

Clause 28: The ambulatory medical device of clauses 26 or 27, wherein when the primary source of power is not able to or is not available to supply electrical power, a secondary source of power provides power to the monitoring and self-test circuitry.

Clause 29: The ambulatory medical device of clause 28, wherein the secondary source of power comprises at least one of a backup battery, a capacitor, an inductor, and a supercapacitor.

Clause 30: The ambulatory medical device of clauses 28 or 29, wherein, responsive to the triggering event when the secondary source of power is providing power to the monitoring and self-test circuitry at least one of: performing a subset of the one or more self-test procedures with power from the secondary source of power, and delay performing the subset of the one or more self-test procedures until the primary source of power is supplying electrical power to the monitoring and self-test circuitry.

Clause 31: The ambulatory medical device of any one of clauses 28-30, wherein the monitoring and self-test circuitry, operating with power from only the secondary source of power, is operational for monitoring during at least one of the following: replacement of the primary source of power, at least one of removal of and donning of the sensing component by the patient for patient showering or bathing; replacement of a garment that comprises the ambulatory medical device worn about a torso of the patient; and replacement of a patient signal sensor.

Clause 32: In another example, an ambulatory medical device comprises: a sensing component to be disposed on a patient for detecting a physiological signal of a patient; one or more components, subsystems, or systems disposed within the ambulatory medical device and operatively coupled to the sensing component; a memory configured to store one or more programs corresponding to one or more predetermined self-tests to be performed on the one or more components, subsystems, or systems; and at least one processor executing a self-test component configured to cause the execution of the one or more programs stored in the memory to perform the one or more predetermined self-tests on the one or more components, subsystems, or systems on a predetermined schedule; wherein the ambulatory medical device is continuously operational during a monitoring period.

Clause 33: The ambulatory medical device of clause 32, wherein the monitoring period begins from when the sensing component is caused to begin the detection of the physiological signal of the patient and ends when the sensing component is caused to no longer detect the physiological signal of the patient.

Clause 34: The ambulatory medical device of clause 32 or 33 further comprising at least one therapeutic element for providing a therapeutic shock to the patient.

Clause 35: The ambulatory medical device of any one of clauses 32-34, wherein the one or more predetermined self-tests comprise at least one of the following battery tests: a battery capacity test, a battery internal resistance test, a battery status test, and a battery charger test.

Clause 36: The ambulatory medical device of any one of clauses 32-35, wherein the one or more predetermined self-tests comprise a power converter test configured to test at least one of an output voltage and a current of a converter, a capacitor charge retention test, and a capacitor charge/discharge test.

Clause 37: The ambulatory medical device of any one of clauses 32-36, wherein the one or more predetermined self-tests comprise a test of response buttons of the ambulatory medical device.

Clause 38: The ambulatory medical device of any one of clauses 32-37, wherein the one or more predetermined self-tests comprise a test of one or more processors of the ambulatory medical device.

Clause 39: The ambulatory medical device of any one of clauses 32-38, wherein the one or more predetermined self-tests comprise a test of at least one of the sensing component and a therapeutic element of the ambulatory medical device.

Clause 40: The ambulatory medical device of any one of clauses 32-39, wherein the one or more predetermined self-tests comprise a test of at least one of a user interface of the ambulatory medical device and a communications module of the ambulatory medical device.

Clause 41: The ambulatory medical device of any one of clauses 32-40, wherein the self-test component is always operational for the one or more predetermined self-tests whether or not a primary source of power is available in the ambulatory medical device.

Clause 42: The ambulatory medical device of clause 41, wherein the primary source of power is a main battery for use with the ambulatory medical device.

Clause 43: The ambulatory medical device of clauses 41 or 42, wherein when the primary source of power is not able to or is not available to supply electrical power, a secondary source of power provides power to the at least one processor.

Clause 44: The ambulatory medical device of clause 43, wherein the secondary source of power comprises at least one of a backup battery, a capacitor, an inductor, and a supercapacitor.

Clause 45: The ambulatory medical device of clauses 43 or 44, wherein, when the secondary source of power is providing power to the at least one processor at least one of performing a subset of the one or more predetermined self-tests with power from the secondary source of power, and delay performing the subset of the one or more predetermined self-tests until the primary source of power is supplying electrical power to the at least one processor.

Clause 46: In an example, an ambulatory medical device comprises: a sensing component to be disposed on a patient for detecting a physiological signal of the patient; and circuitry comprising a monitoring component for detecting a triggering event, and a self-test component for executing one or more self-tests procedures on the ambulatory medical device, wherein the ambulatory medical device is always operational during a monitoring period.

Clause 47: The ambulatory medical device of clause 46, wherein the monitoring period begins from when the sensing component is caused to begin the detection of the physiological signal of the patient and end when the sensing component is caused to no longer detect the physiological signal of the patient.

Clause 48: The ambulatory medical device of clauses 46 or 47, further comprising a therapeutic element for delivering electrotherapy to the patient.

Clause 49: The ambulatory medical device of any of clauses 46-48, wherein the ambulatory medical device comprises a garment worn about a torso of the patient.

Clause 50: In another example, a continuous-use medical device comprises: a sensing component for detecting a physiological signal of a patient; a memory; and a processor operatively connected to the sensing component and the memory, the processor configured to detect at least one of an impact and a vibration event experienced by the continuous-use medical device; and in response to detecting the at least one of the impact and the vibration event experienced by the continuous-use medical device, store a flag in the memory of the continuous-use medical device.

Clause 51: The continuous-use medical device of clause 50, wherein the flag is configured to be retrieved from the memory when continuous use of the continuous-use medical device ends.

Clause 52: The continuous-use medical device of clauses 50 or 51, wherein the flag, when retrieved from the memory, provides an indication that at least one of an impact and a vibration event occurred.

Clause 53: The continuous-use medical device of clause 52, wherein the indication is displayed on at least one display device along with information associated with the indication to allow for review of the indication and the information by service personnel.

Clause 54: The continuous-use medical device of any of clauses 50-53, wherein the at least one of the impact and the vibration event experienced by the continuous-use medical device corresponds to one of an impact level that exceeds a predetermined impact level and a vibration level that exceeds a predetermined vibration level.

Clause 55: The continuous-use medical device of any of clauses 50-54, wherein at least one of the impact and the vibration event experienced by the continuous-use medical device corresponds to an impact duration that exceeds a predetermined impact duration and a vibration duration that exceeds a predetermined vibration duration.

Clause 56: The continuous-use medical device of any of clauses 50-55, further comprising an electromechanical switch for detecting the at least one of the impact and the vibration event experienced by the continuous-use medical device.

Clause 57: The continuous-use medical device of any of clauses 50-56, further comprising at least one of a single axis accelerometer, a multi-axis accelerometer, and a piezoelectric transducer for detecting the at least one of the impact and the vibration event experienced by the continuous-use medical device.

Clause 58: The continuous-use medical device of any of clauses 50-57, wherein the processor is further configured to, in response to detecting the at least one of the impact and the vibration event experienced by the continuous-use medical device, initiate one or more self-tests of the continuous-use medical device.

Clause 59: The continuous-use medical device of clause 58, wherein the one or more self-tests comprise tests of one or more devices, components, and subsystems of the continuous-use medical device to ensure that the at least one of the impact and the vibration event has not adversely affected any of the one or more devices, components, and subsystems.

Clause 60: In an example, an ambulatory medical device comprises: a sensing component to be disposed on a patient for detecting a physiological signal of the patient; and circuitry comprising a monitoring component for monitoring for a triggering event, and a self-test component for executing one or more self-test procedures on the ambulatory medical device, wherein the monitoring component is always operational for monitoring during a period beginning from when the physiological signal of the patient is first sensed by the sensing component and ending when the monitoring is no longer needed for the patient.

Clause 61: The ambulatory medical device of clause 60, wherein the physiological signal can comprise a cardiac signal.

Clause 62: The ambulatory medical device of clauses 60 or 61, wherein the device can further comprise a therapeutic element for delivering therapy to the patient.

Clause 63: The ambulatory medical device of any one of clauses 60-62, wherein the therapy can comprise electrotherapy Clause 64: The ambulatory medical device of any one of clauses 60-63, wherein the continuous-use medical device can comprise a garment worn by the patient.

Clause 65: The ambulatory medical device of any one of clauses 60-64, wherein the physiological signal of the patient can first be sensed when the physiological signal is either; acquired by the sensing component; received from the sensing component by a processing component that is configured to process the physiological signal; processed by the processing component for the purpose treatment analysis; or stored in a memory.

Clause 66: The ambulatory medical device of any one of clauses 60-65, wherein the monitoring is no longer needed for the patient upon the occurrence of one or more of the following events: the patient being implanted with sensing and monitoring components; a changed physical condition of the patient whereupon the patient is medically required to use a different medical device; the patient being switched to a different device having more or fewer functions; the patient being switched to a different device used by a different caregiver; and the patient being moved from one environment to another.

Clause 67: The ambulatory medical device of any one of clauses 60-66, wherein the monitoring component can be operational for monitoring during at least one of the following: changing of a power source of the ambulatory medical device; removal of and donning of the sensing component by patient for patient showering or bathing; replacement of a garment that comprises the ambulatory medical device worn about a torso of the patient; and replacement of a patient signal sensor.

Clause 68: The ambulatory medical device of any one of clauses 60-67, wherein replacement of the patient signal sensor can be in response to wear of the patient signal sensor over a time due to use.

Clause 69: In another example, an ambulatory medical device comprises: a sensing component to be disposed on a patient for detecting a physiological signal of the patient; and circuitry configured to detect a change in a software or firmware configuration of the ambulatory medical device, and a self-test component for, in response to the change in the software configuration, executing one or more self-tests procedures on the ambulatory medical device.

Clause 70: The ambulatory medical device of clause 69, wherein the change in the software configuration can comprise a software or firmware update to the software of the ambulatory medical device.

Clause 71: The ambulatory medical device of clauses 69 or 70, wherein the change in the software or firmware configuration can comprise an update to one or more device parameters set in the ambulatory medical device.

Clause 72: In another example, an ambulatory medical device comprises: a sensing component to be disposed on a patient for detecting a physiological signal of the patient; and circuitry comprising a monitoring component for monitoring for a triggering event, and a self-test component for executing one or more self-test procedures on the ambulatory medical device, wherein the monitoring component is always operational for the monitoring whether or not a primary source of power is available in the ambulatory medical device.

Clause 73: The ambulatory medical device of clause 72, wherein the primary source of power can be a main battery for use with the ambulatory medical device.

Clause 74: The ambulatory medical device of clauses 72 or 73, wherein, when the primary source of power is not able to or is not available to supply electrical power, a secondary source of power can provide power to the monitoring component.

Clause 75: The ambulatory medical device of any one of clauses 72-74, wherein the secondary source of power can comprise a battery, a capacitor, a supercapacitor, an inductor, or other energy storage device.

Clause 76: The ambulatory medical device of any one of clauses 72-75, wherein, responsive to the triggering event when the secondary source of power is providing power to the monitoring component, the self-test component can: (a) perform a first subset of the one or more self-test procedures with power only from the secondary source of power, or can (b) delay performing a second subset of the one or more self-test procedures until the primary source of power is supplying electrical power to the monitoring component.

Clause 77: The ambulatory medical device of anyone of clauses 72-76, wherein the first and second subsets of self-test procedures can be the same or different.

Clause 78: The ambulatory medical device of anyone of clauses 72-77, wherein step (a) or step (b)(of clause 76) can be performed for a period of time when the primary source of power is not able to or is not available to supply electrical power to the first component that is at least one week or at least one month.

Clause 79: The ambulatory medical device of any one of clauses 72-78, wherein the monitoring component can be operative for directly or indirectly monitoring for the triggering event.

Clause 80: The ambulatory medical device of any one of clauses 72-79, wherein the monitoring component can indirectly monitor for the occurrence of the event via a component, subsystem, or system that is configured to convert the event into a form for processing by the monitoring component.

Clause 81: The ambulatory medical device of any one of clauses 72-80, wherein the monitoring component can comprise one or more microprocessors, microcontrollers, or other integrated device.

Clause 82: The ambulatory medical device of any one of clauses 72-81, wherein the monitoring component, operating with power from only the secondary source of power, can be operational for monitoring during at least one of the following events: replacement of the primary source of power, removal of and donning of the sensing component by patient for patient showering or bathing; replacement of a garment that comprises the ambulatory medical device worn about a torso of the patient; and replacement of a patient signal sensor (e.g., due to wear over a period of time).

Clause 83: In another example, an ambulatory medical device comprises: a sensing component to be disposed on a patient for detecting a physiological signal of the patient; and circuitry comprising a monitoring component for monitoring for a triggering event, and a self-test component for executing one or more self-test procedures on the ambulatory medical device, wherein the monitoring component is always operational for the monitoring during a period beginning from when the sensing component is first configured to begin the detection of the physiological signal of the patient and ending when the sensing component is no longer detecting the physiological signal of the patient.

Clause 84: The ambulatory medical device of clause 83, wherein the device can further comprise a therapeutic element for delivering electrotherapy to the patient.

Clause 85: The ambulatory medical device of clauses 83 or 84, wherein the continuous-use medical device can comprise a garment worn about a torso of the patient.

Clause 86: In another example, an ambulatory medical device comprises: a monitoring component for monitoring for one or more triggering events different from an intended medical use of or intended medical purpose for the medical device that could potentially prevent the medical device from functioning for its intended purpose; and a self-test component responsive to the one or more triggering events for executing one or more self-tests procedures on the ambulatory medical device.

Clause 87: The ambulatory medical device of clause 86, wherein the one or more triggering events can include: excessive mechanical shock; exposure to temperature greater than a predetermined maximum temperature or less than a predetermined minimum temperature; exposure to excessive moisture; excessive strain on a component, subsystem, or system of the medical device; exposure to a temperature change outside of predetermined limits; exposure to a rate of temperature change outside of predetermined limits; prolonged vibration outside a time limit or an amplitude limit; passage of time beyond a predetermined limit; or a change in ambient pressure beyond a predetermined limit.

Clause 88: In another example, a continuous-use medical device comprises: one or more components, subsystems, and/or systems; a user interface; a memory storing one or more programs for testing the one or more components, subsystems and/or systems; and a processing element operatively coupled to the user interface, the one or more components, subsystem and/or systems, and the memory, the processing element responsive to a triggering event for executing a subset of the one or more programs selected via the user interface.

Clause 89: The continuous-use medical device of clause 88, wherein the subset of the one or more programs can be selected before the triggering event.

Clause 90: In another example, a continuous-use medical device comprises: one or more components, subsystems, and/or systems; an impact detector; a memory storing one or more programs for testing the one or mom components, subsystems, and/or systems; and a processing element operatively coupled to the memory, the impact detector, and the one or more components, subsystems, and/or systems, the processing element operative for executing the one or more programs in response to detecting via the impact detector an impact greater than a predetermined impact stored in the memory.

Clause 91: The continuous-use medical device of clause 90, wherein the impact detector can comprise a piezoelectric transducer, a single axis accelerometer, or a multi-axis accelerometer.

BRIEF DESCRIPTION OF THE DRAWINGS

These and other features and characteristics of the present disclosure, as well as the methods of operation and functions of the related elements of structures and the combination of parts and economics of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 8 is a non-exhaustive list of example triggering events for self-tests;

FIG. 9 is a non-exhaustive list of example self-tests; and

DETAILED DESCRIPTION OF THE INVENTION

Figure 1:
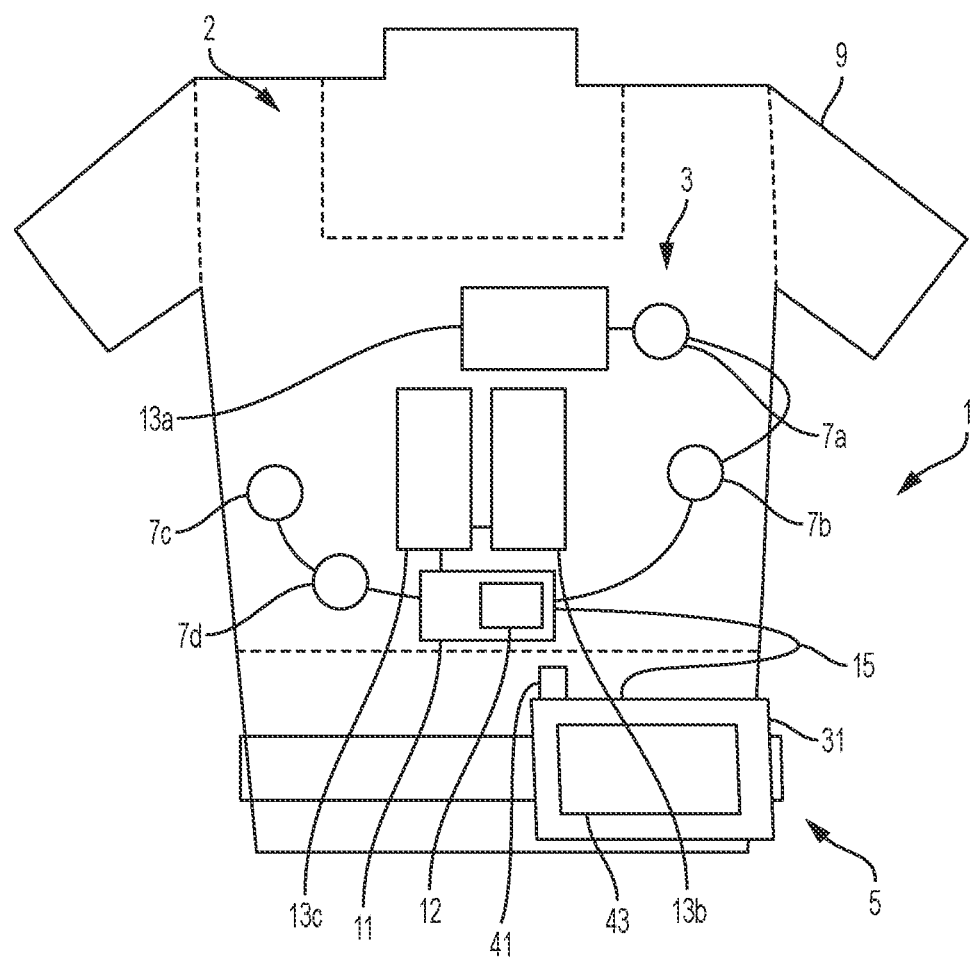
FIG. 1 shows an example wearable medical device.

As used herein, the singular form of "a", "an", and "the" include plural referents unless the context clearly dictates otherwise.

As used herein, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention can assume various alternative orientations and, accordingly, such terms are not to be considered as limiting. Also, it is to be understood that the invention may assume various alternative variations and stage sequences, except where expressly specified to the contrary. It is also to be understood that the specific devices and processes illustrated in the attached drawings, and described in the following specification, am examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention am approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between. e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This may refer to a direct or indirect connection that may be wired and/or wireless in nature. Additionally, two units or components may be in communication with each other even though the data transmitted may be modified, processed, routed, and the like, between the first and second unit or component. For example, a first unit may be in communication with a second unit even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible.

This disclosure relates to tests performed in and/or on medical devices. For example, tests as disclosed herein can be performed in and/or on medical devices that are configured to be substantially always on or for continuous use (after initially being powered-on) for a predetermined medical purpose. For example, such medical devices can include monitoring devices configured to continuously monitor a patient for certain medical conditions for extended periods of time, for example, for over 4 hours (e.g. treatment and monitoring devices such as sleep apnea devices), over 12 hours (e.g. treatment and/or monitoring devices such as mobile cardiac monitoring devices, wearable defibrillator devices, etc.), and including for substantially continuous monitoring over time periods over 24 hours or even several days. Such devices may monitor the patient substantially continuously, aside from periods during which the patient may periodically remove the device, such as for showering, refitting, changing a component of the device, etc. In some implementations, such devices are capable of, in additional to monitoring for medical conditions, providing treatment to a patient based on detecting a predetermined medical condition. For example, medical devices as disclosed herein can include automated always- or continuously-on (or continuous-use) defibrillators, such as in-facility defibrillators (e.g., for patients that are confined to a limited space within a facility, such as, within a hospital environment, to a patient's room) or outpatient wearable defibrillators. Such devices can be configured to monitor a patient for an arrhythmia condition such as ventricular tachycardia (VT) or ventricular fibrillation (VF). If the arrhythmia condition is detected, the device can automatically provide a defibrillation pulse or shock to treat the condition.

Other example devices capable of performing or running the tests and techniques discussed herein include automated always- or continuously-on portable defibrillators for use in certain specialized conditions and/or environments such as in combat zones or within emergency vehicles. Such devices may need to remain always powered ON so that they may be used immediately (or substantially immediately) in a life-saving emergency. In some examples, the automated extended-use defibrillators described herein can be pacing-enabled, e.g., capable of providing therapeutic pacing pulses to the patient.

For example, a continuous-use medical device as described herein can include at least one component, subsystem, or system (e.g., powered or unpowered circuitry or one or more processors) that is substantially always enabled during a predefined period or in a state that is available for immediate (or substantially immediate) use for at least one of the device's primary uses as discussed in further detail below. For example, in the case of certain treatment and monitoring devices such as sleep apnea devices the predefined period over which the devices may substantially continuously monitor for certain sleep apnea-related conditions may be over 4 hours. In the case of certain other treatment and/or monitoring devices such as mobile cardiac monitoring devices, ambulatory and/or wearable defibrillator devices, such predefined period may be over 12 hours. These devices can be configured for substantially continuous monitoring over time periods over 24 hours or even several days. As noted, such devices may monitor the patient substantially continuously, aside from periods during which the patient may periodically remove the device, such as for showering, refitting, changing a component of the device, etc.

For example, medical devices that can implement one or more of the features described herein can be invasive (e.g., an implantable defibrillator and/or pacing device) or non-invasive (e.g., a wearable defibrillator). For example, the medical device may be ambulatory, e.g., the device is capable of and designed for moving with the patient.

Example Medical Device

In an example and with reference to FIG. 1, the medical device can be configured as a wearable defibrillator, denoted generally as reference numeral 1, such as the LifeVest® wearable defibrillator available from ZOLL® Medical Corporation of Pittsburgh, PA and Chelmsford, MA. The wearable defibrillator 1 can be worn by a patient and can include a garment, generally denoted as reference numeral 2, an electrode assembly, denoted generally as reference numeral 3, and a monitor, denoted generally as reference numeral 5, operatively connected to the electrode assembly 3. The garment 2 can be configured as a harness, shirt, or other apparel and is configured to permit the patient to wear the defibrillator 1. The electrode assembly 3 can be configured to be assembled within the garment 2.

Such wearable defibrillators can be typically worn nearly continuously for two to three months at a time. During the period of time in which they are worn by the patient, the wearable defibrillator 1 can be configured to continuously monitor the vital signs of the patient, to be user-friendly and accessible, to be as light-weight, comfortable, and portable as possible, and to be capable of delivering one or more life-saving therapeutic shocks when needed. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944, the entirety of all of which are incorporated by reference herein.

With continued reference to FIG. 1, the electrode assembly 3 includes a plurality of electrodes, such as electrodes 7a, 7b, 7c, and 7d, which contact a patient 9 when the wearable defibrillator 1 is worn by the patient 9. According to one example, the electrodes 7a, 7b, 7c, and 7d are configured to receive ECG signals from the patient 9. For instance, the electrodes 7a, 7b, 7c, and 7d can be positioned on the patient 9 to receive ECG signals from a front-to-back channel and from a side-to-side channel. For example, the front-to-back (FB) channel can include one of electrodes 7a, 7b, 7c, and 7d positioned on the chest of the patient 9 and another one of the electrodes 7a, 7b, 7c, and 7d positioned on the back of the patient 9. For example, the side-to-side (SS) channel includes one of the electrodes 7a, 7b, 7c, and 7d positioned on the left side of the chest and another one of the electrodes 7a, 7b, 7c, and 7d positioned on the right side of the chest of the patient 9. In some examples, the electrodes 7a, 7b, 7c, and 7d can be operatively connected to a distribution node 11 of the electrode assembly 3.

In some implementations, the electrode assembly 3 can also comprise therapy pads 13a, 13b, and 13c operatively connected to the distribution node 11. The therapy pads 13a, 13b, and 13c can be configured to deliver one or more life-saving therapeutic shocks when needed. In some examples, the electrode assembly 3 can also include other sensing electrodes and devices (not shown) such as, but not limited to, heart beat sensors, accelerometers, and sensors capable of measuring blood pressure, heart rate, thoracic impedance, respiration rate, heart sounds, acoustic sensors, audio transducers, and the activity level of the subject. The electrode assembly 3 can further comprise a tactile stimulator 12, such as a vibrator, positioned within the distribution node 11 to provide tactile stimulation to the patient 9 as described in greater detail hereinafter.

The monitor 5 can be operatively connected to one or mom of the therapy pads 13a, 13b, and 13c and electrodes 7a, 7b, 7c, and 7d via, e.g., a trunk cable 15 or any other suitable cable or connection device. Wiring or other connection devices can be used to connect at least one portion of the distribution node 11 to the electrodes 7a, 7b, 7c, and 7d and therapy pads 13a, 13b, and 13c. Alternatively, the monitor 5 can be operatively connected to one or more of the electrodes 7a, 7b, 7c, and 7d, therapy pads 13a, 13b, and 13c, and distribution node 11 by a wireless connection or a combination of wireless and wired connections.

The distribution node 11 is configured to obtain ECG data from the electrodes 7a, 7b, 7c, and 7d, digitize this data, and transfer this data to the monitor 5. Accordingly, the distribution node 11 includes a processor, such as a belt node processor (BNP) 17 (see FIGS. 3, 4A, and 4B), operatively connected to electrodes 7a, 7b, 7c, and 7d and configured to receive signals representing the ECG of the patient 9 from the electrodes 7a, 7b, 7c, and 7d. The BNP 17 communicates with the monitor 5 via a Controller Area Network (CAN) bus 19 (see FIGS. 4A and 4B) or any other suitable bus that comprises trunk cable 15. The BNP 17 is also configured to sense whether one or more of electrodes 7a, 7b, 7c, and 7d have fallen off the patient's body, to control the tactile stimulator 12, and to fire the electrode gel interface for providing electrolytic gel to the therapy pads 13a, 13b, and 13c when a request is received from the monitor 5.

Figure 2:
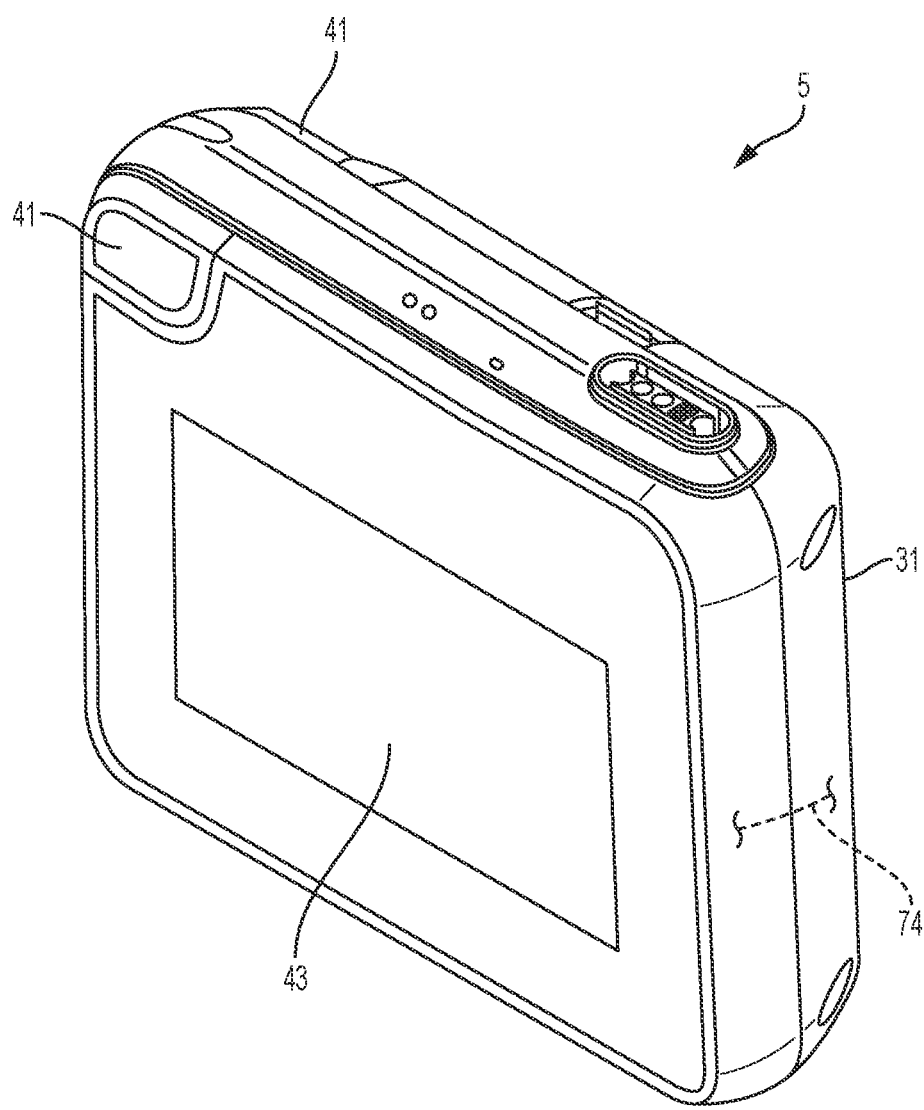
FIG. 2 shows a front perspective view of an example monitor for a wearable medical device.

With reference to FIG. 2 and with continuing reference to FIG. 1, the monitor 5 can include an external housing 31 having a port to which the ECG electrodes 7a, 7b, 7c, and 7d and therapy pads 13a, 13b, and 13c of the electrode assembly 3 are operatively coupled to the monitor 5 via the trunk cable 15. The monitor can include one or more batteries, such as a rechargeable and removable battery (not shown) positioned within a battery housing. The battery has sufficient capacity to allow the wearable defibrillator 1 to administer one or more therapeutic shocks as well as provide power to all of the internal components of the defibrillator 1. The external housing 31 further comprises at least one, and for example, a pair of patient response buttons 41 positioned, for example, in the top left corner of the housing 31. The external housing 31 of the defibrillator can also include a display screen 43 for providing information to the patient 9 and for providing a user input device to the patient 9. Further details of the monitor 5 can be found in U.S. patent application Ser. No. 14/448,997, which is hereby incorporated by reference in its entirety.

System Architecture of an Example Medical Device

Figure 3:
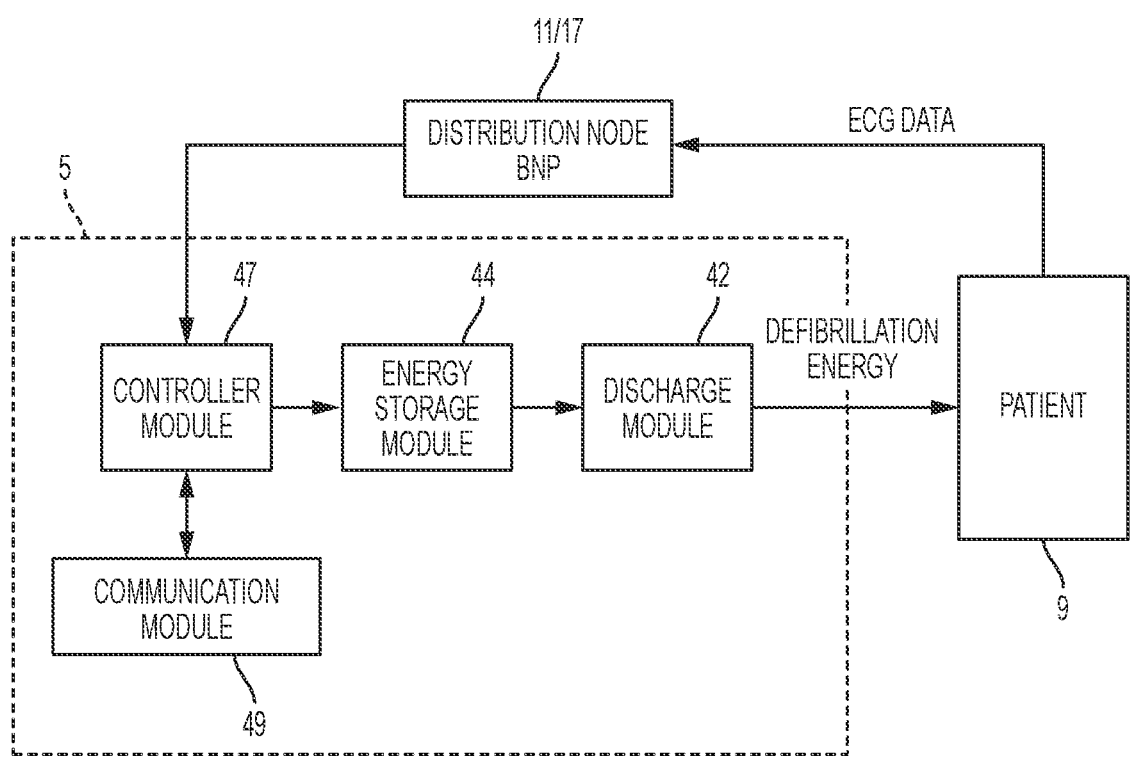
FIG. 3 is an example block diagram illustrating the manner in which functional components of the wearable medical device may interact.

With reference to FIG. 3 and with continuing reference to FIGS. 1 and 2, the functional components of the monitor 5 can be provided within the external housing 31 of the monitor 5. In one example, the functional components can be provided on a distributed printed circuit board as disclosed in U.S. patent application Ser. No. 14/448,857, which is hereby incorporated by reference in its entirety. In one example, the functional components can comprise a discharge module 42, an energy storage module 44, a controller module 47, and a communication module 49. The discharge module 42 is for selectively delivering an energy pulse to the patient 9 via therapy pads 13a, 13b, and 13c. The energy storage module 44 can be operatively connected to the discharge module 42. The controller module 47 can be operatively connected to the energy storage module 44 and can be configured to control the delivery of the energy pulse to the patient 9. The communication module 49 can be operatively connected to the controller module 47.

In one example, the energy storage module 44 can include a high voltage power convertor 64 (shown in FIG. 4) and a capacitive device, such as a bank of capacitors 67 (shown in FIG. 4). The discharge module 42 can include at least one high-voltage switch (not shown) and can be configured to selectively deliver an energy pulse stored in the energy storage module 44 to the patient 9 based on a signal from the controller module 47. The energy pulse is sent from the discharge module 42 through a port to the patient 9 via therapy pads 13a, 13b, and 13c.

A biphasic waveform is delivered to the patient 9 by switching the at least one high voltage switch of the discharge module 42. The operation of the pulse delivery system can be dynamic and depend on the patient's body impedance while the pulse is being delivered. For example, an amount of energy delivered can be held constant while varying the duration of the first phase and the second phase. In another example, a monophasic waveform can be delivered to the patient depending on the patient's condition.

Figure 4A:
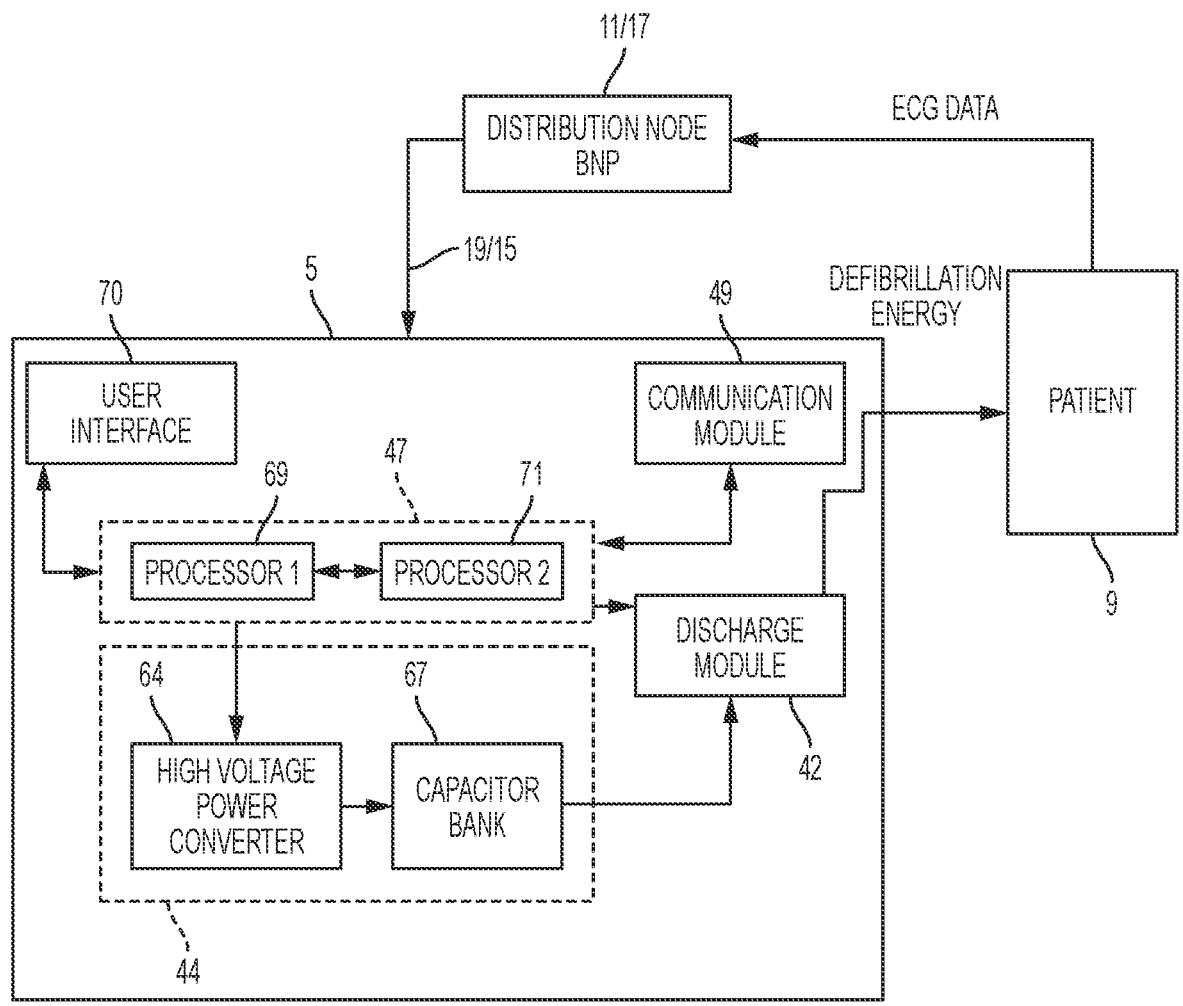
FIGS. 4A-B illustrate example block diagrams of a wearable medical device.
Figure 4B:
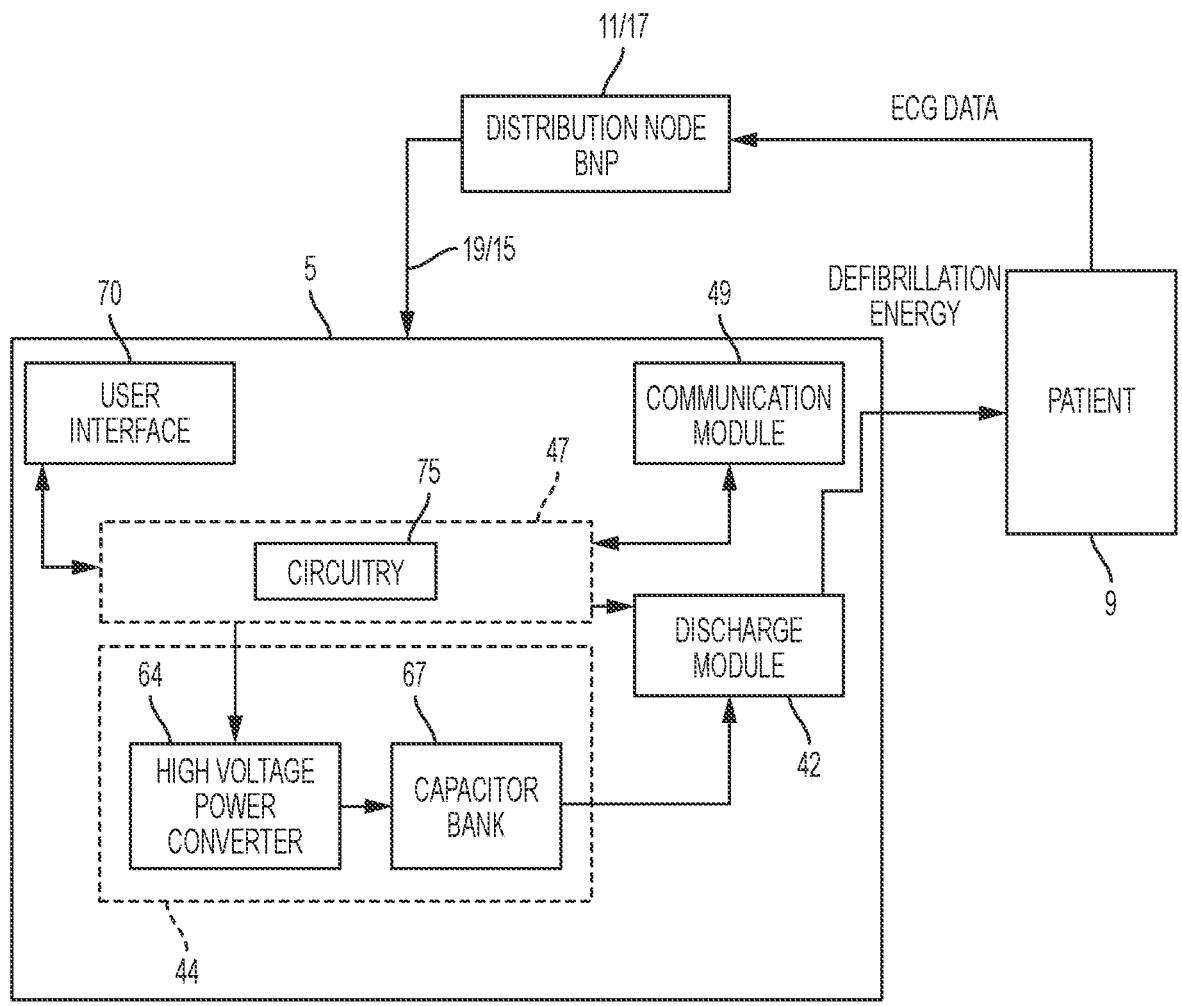

With reference to FIGS. 4A-4B, and with continuing reference to FIGS. 1-3, controller module 47 can include one or more processors 69, 71 (FIG. 4A) each of which operates under the control of a control program that executes at runtime for performing certain functionalities of the wearable defibrillator 1. In one example, controller module 47 can include at least a first processor 69 and a second processor 71. In one example, the first processor 69 and the second processor 71 can be configured to function as disclosed in U.S. Pat. No. 8,904,214, which is hereby incorporated by reference in its entirety.

In some implementations, one of the first and second processors 69,71 may be a multi-core processor. The interface between the processors 69, 71 can be implemented as a serial interface. For example, the first processor 69 can be configured to include an operating system (e.g., accessible via a shell) and include one or more programs for controlling the overall continuous-use device, including its various components, subsystems, and systems. For example, in a continuous-use defibrillator, the second processor 71 can be configured to manage and operate the high voltage circuitry used to deliver, monitor, and modify one or more defibrillation pulses to the patient. In this regard, for example, the second processor 71 can be configured to run as a slave to the first processor 69. As such, a monitoring component and a self-test component as described herein can be executed within the first processor 69 and make use of shell features to interact with various other device components, subsystems, and systems.

Also, or alternatively to processors 69, 71, controller module 47 (FIG. 4B) can include discrete and/or integrated electrical and/or electronic circuitry 75 that is configured to perform the functions described herein (either alone or in combination with one or more of processors 69, 71), but not under the control of a control program. In an example, the electrical and/or electronic circuitry 75 of controller module 47 can include one or mom discrete elements, such as, without limitation, one or more of the following discrete elements: transistor, resistor, capacitor, inductor, memristor, diode, loudspeaker, buzzer, linear variable differential transformer (LVDT), rotary encoder, shaft encoder, inclinometer, motion sensor, vibration sensor, flow meter, strain gauge, accelerometer, thermocouple, thermopile, thermistor, resistance temperature detector (RTD), bolometer, thermal cut-off, magnetometer, gauss meter, hygrometer, photo resistor. LED or other light emitting device, and/or antenna.

In an example, the electrical and/or electronic circuitry 75 of controller module 47 can also or alternatively include one or more integrated circuits, such as, without limitation, analog integrated circuit, digital integrated circuit, mixed signal (analog and digital) integrated circuit, application specific integrated circuit (ASIC), programmable logic device (PLD), gate array, field programmable gate array (FPGA), and/or microelectromechanical systems (MEMS). In an example, these one or more integrated circuits can include one or more of analog-to-digital converter (ADC), a multiplexer, a power regulator, or some combination thereof.

In another example, controller module 47 is operatively connected to a user interface 70 (comprised of one or more response buttons 41 and/or display screen 43), the high voltage power convertor 64, and the discharge module 42. Such a configuration allows at least one of the first processor 69 and the second processor 71 to be capable of providing output to a patient 9, for example through the display screen 43, and accept input from the patient 9, for example from response buttons 41, as well as provide instructions to the high voltage power converter 64 and/or the discharge module 42 to deliver a therapeutic shock to the patient 9. For example, the first processor 69 and the second processor 71 shown in FIG. 4A or circuitry 75 shown in FIG. 4B can be used to provide certain functionality within the wearable defibrillator 1 such as, but not limited to: high voltage converter control; discharge module control; real time clock (date/time) for the system; execution of timing-critical software or functions such as therapy pulse synchronization (e.g., synchronizing the pulse delivery to avoid delivering a pulse on a T wave); ECG acquisition from the CAN bus 19; ECG monitoring and arrhythmia detection; user interface control; treatment sequencing; audio message generation; and data communications and storage. An example of the methods used to detect abnormal heart rhythms can be found in U.S. Pat. No. 5,944,669, which is assigned to the assignee of the present application and which is hereby incorporated by reference in its entirety. These functionalities can be performed by circuitry 75 distributed between the two processors 69 and 71, or some combination of circuitry 75 and one or more of processors 69 and 71. For example, the first processor 69 can perform certain ones of these functionalities while others of the functionalities can be performed by the second processor 71.

In some implementations, the BNP 17 can be operatively connected to the controller module 47. The BNP 17 can act as an ECG data acquisition engine for the controller module 47 via the CAN bus 19 as described hereinabove.

In one example, the communication module 49 can be controlled by at least one of the processors 69, 71 or circuitry 75 of the controller module 47 and can provide various devices for communicating information to and from the monitor 5. For instance, the communication module 49 can include a GPS transceiver, a Bluetooth transceiver, a Wi-Fi modem, and a cellular modem. The communication module 49 is configured to communicate with a remote server provided via the cellular modem. Alternatively, if cellular communication capabilities are not available, the communication module 49 can communicate with the remote server via the Wi-Fi modem.

For the purpose of simplicity, hereinafter the invention will be described with reference to monitor 5 shown in FIG. 4A that includes controller module 47 having processors 69, 71. However, this is not to be construed as limiting the invention since it is envisioned that controller module 47 can, also or alternatively to processors 69, 71, include circuitry 75.

Figure 5:
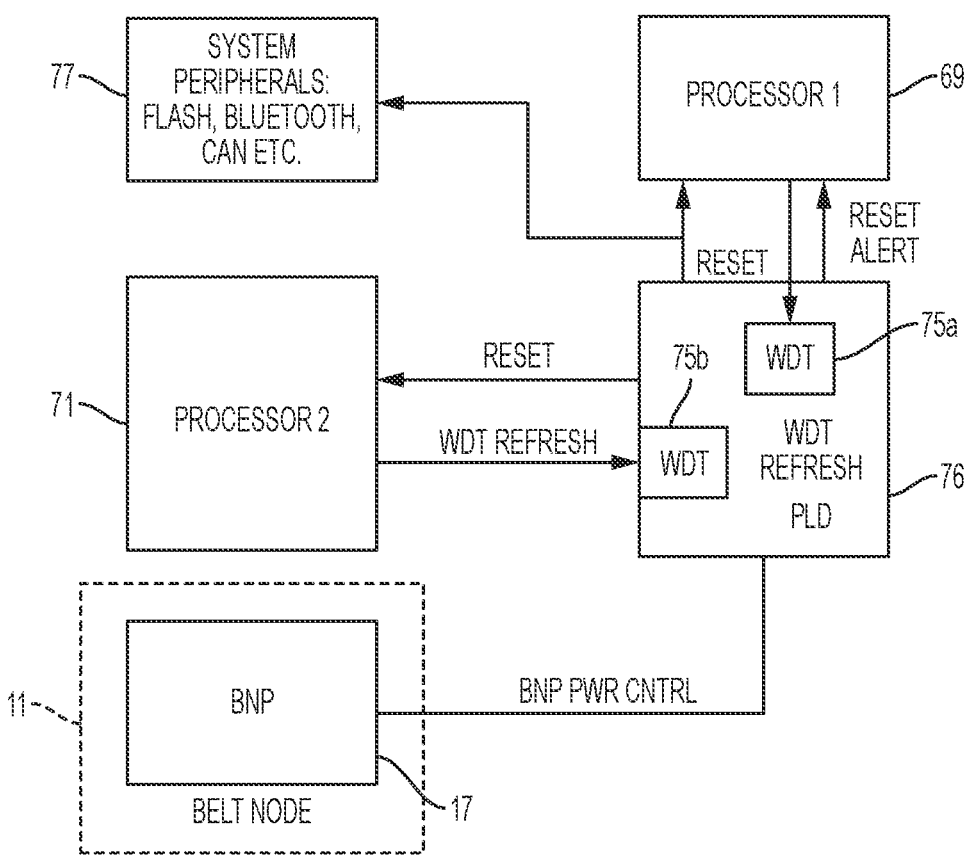
FIG. 5, is an example block diagram of a supervisory, e.g., watchdog timer (WDT) scheme for a wearable medical device.

With reference to FIG. 5 and with continuing reference to FIGS. 4A and 4B, in one example, the controller module 47 can include circuitry or circuit 76, e.g., implemented on a programmable logic device (PLD), to provide, among other things, a supervisory circuit function. The circuit 76 can be configured to provide interfacing support and input/output translations between the first processor 69, the second processor 71, and various system peripherals 77. The circuit 76 can be configured to implement a processor supervisory function. For example, such a supervisory function can be a watchdog timer (WDT) function 75a, 75b. In general, the supervisory function can monitor one or all three of the first processor 69, the second processor 71, and the BNP 17. In one example, the first processor 69 and the second processor 71 can be required to periodically service the WDT 75a, 75b function to prevent a timeout from occurring.

Operation of the Example Medical Device

Figure 6:
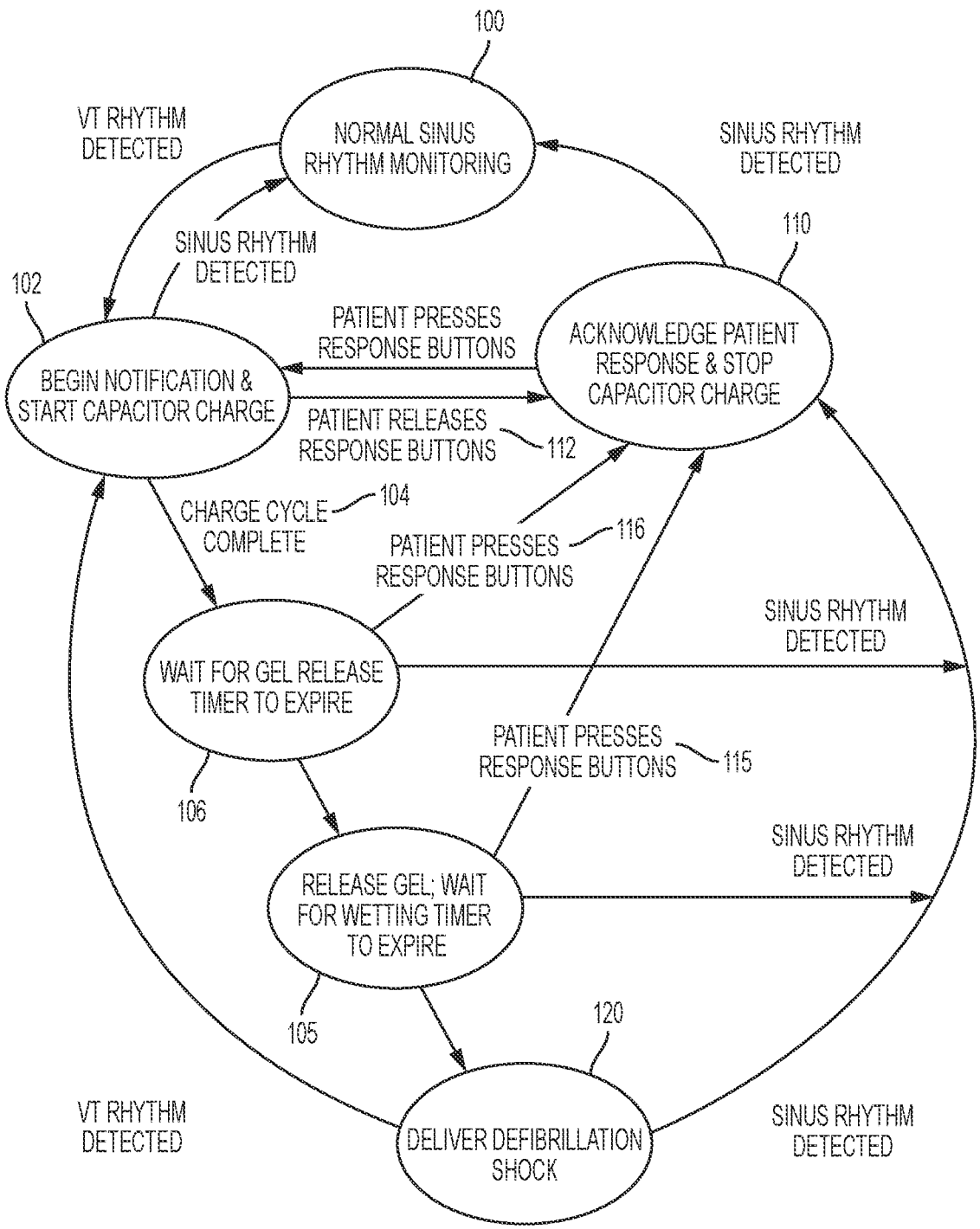
FIG. 6 is an example flow chart of a method of operation of a wearable medical device.

With reference to FIG. 6, a description of the manner in which the monitor 5 operates when an abnormal event is detected by the detection algorithm of one or both of the processors 69, 71 will be described. Initially, at least one of the processors 69, 71 is running the detection algorithm and detecting normal sinus rhythm at 100. In one example, one of the processors 69, 71 can be running the detection algorithm and the other of the processors 69, 71 can be in a low-power sleep state. When the detection algorithm detects a VT or VF rhythm type, it dispatches an event to the state machine that is run on at least one of the processors 69, 71. The state machine exits the Normal Sinus Rhythm Monitoring state 100 when the event is received and transitions to a notification state 102 that begins the patient notification sequence to provide stimuli to the patient to make the patient aware that an event has been detected and starts a capacitor charge cycle. After the capacitors are fully charged a Charge Cycle Complete event 104 can be sent to at least one of the processors 69, 71. As shown in FIG. 6, a timer can be used to determine when to release the gel (see 106) and allow timing of a gel wetting period (see 105) to reduce transthoracic impedance.

At any point after the notification state 102, the patient can cancel the treatment sequence by pressing the response buttons 41 and the system acknowledges the patient response and stops charging capacitors 110. This is shown by arrows 112, 115, and 116. If the patient does not respond to the alarms and the timer for gel wetting expires, the state machine issues a command 120 to at least one of the processors 69, 71 to fire the defibrillator and treat the patient. Since at least one of the processors 69, 71 is continuously monitoring the patient's rhythm, the at least one processor 69, 71 can detect a sinus rhythm if the defibrillation was successful and send an event notification to the state machine.

An automated continuous-use medical device as described herein, such as wearable defibrillator 1, can be used for monitoring and, optionally, treating a patient. For example, the automated continuous-use medical device can be designed to be always-on and configured to perform one or more self-tests, including, without limitation, one or more event-driven self-tests, one or more periodic self-tests, one or more aperiodic self-tests, or some combination thereof. Non-limiting examples of such self-tests will now be described with reference to a continuous-use defibrillator that is used for monitoring an ambulatory patient and delivering a shock when necessary. However, the disclosure herein of wearable defibrillator 1 is not to be construed as limiting the disclosure in any manner as it is envisioned that the present invention can also be utilized with any medical device that is designed to be always on for monitoring and, optionally, treating a patient.

In general, in a continuous-use medical device that is used for monitoring an ambulatory patient and delivering a shock when necessary, one or more circuits or processors (e.g., under the control of programs stored in a memory accessible to the one or more processors) of the medical device can perform one or more of the self-tests described herein based on a triggering event such as, but not limited to, one or mom triggering events.

In an example, the continuous-use medical device can include one or more monitoring elements or components, e.g., circuitry or processors, which are always operational and monitoring for triggering events throughout an expected period of use of the device by a patient as described in further detail below. For example, in certain implementations, one or more monitoring components can be always operational throughout a life span of the continuous-use device.

In some implementations, one or more monitoring elements can include non-powered elements, e.g., elements that do not require external power to operate. For example, such an element can include a mechanical switch that can detect an impact on the device or other device abuse, and change its state from ON to OFF (or vice-versa). Such a change in state can cause a self-test to be executed by the continuous-use medical device. Alternatively, as detailed below, a low power microprocessor can be configured to be always operational in a monitoring state regardless of the primary power status of the medical device.

In implementations, the continuous-use medical device can include one or mom self-testing components that can execute one or more self-tests based on the triggering events. For example, such self-testing components can include circuitry and/or processors that may be always operational throughout an expected period of use of the device as described below. In some examples, one or more of the monitoring and self-testing components can be included in the monitor 5 (see, e.g., FIG. 1) of a wearable defibrillator. Further, it should be apparent to a person skilled in the art that aspects of the monitoring elements and the self-testing components can be together included in a single circuit or microprocessor or distributed over multiple circuits or microprocessors.

One or more examples described below in connection with triggering events for self-tests and self-tests performed by the medical device are with specific reference to a microprocessor as an example of circuitry that can perform in the manner discussed in the example. However, this is not to be construed as limiting the invention since it is envisioned that the microprocessor mentioned in any such example can be replaced with any suitable and/or desirable circuit or circuitry that can perform the operation(s) disclosed in the example.

Certain example triggering events are described below in the context of an example continuous-use defibrillator. It should be understood that these examples are equally applicable to other continuous-use medical devices, including continuous-use cardiac monitoring devices, or therapeutic devices, e.g., devices configured for therapeutic electrical current delivery such as pacing, and/or TENS (transcutaneous electrical nerve stimulation).

In an example, the circuitry 75 of the controller module 47 of the continuous-use medical device is configured to detect a triggering event as described in further detail below. As discussed hereinabove, the triggering event may be any number of events detected by any number of sensors associated with the continuous-use medical device. For example, the triggering event may be the detection of an impact above a predetermined threshold on the continuous-use medical device by an impact detector, such as a piezoelectric transducer, a mechanical switch, a single axis accelerometer, or a multi-axis accelerometer. This impact may be due to the continuous-use medical device being dropped by the patient, for example. In another example, the triggering event may be a detection of the sensing electrodes being removed from contact with the patient or detection of a temperature in excess of a predetermined maximum temperature or less than a predetermined minimum temperature by a temperature sensor associated with the continuous-use medical device. In yet another example, the triggering event may be any one or more of the triggering events listed in FIG. 8.

In one example, the continuous-use medical device may be configured to detect one or more of the triggering events and set a flag in the memory of the continuous-use medical device that the one or more triggering event occurred. Depending on predefined rules in a program stored in a memory of the continuous-use device, the device may or may not initiate a self-test in response to the triggering event. This flag can be configured to be retrieved by service personnel, for example, when continuous-use of the medical device is deemed to have ended. These flags are configured to provide an indication to the service personnel of particular events that occurred during patient use of the continuous-use medical device and allow the service personnel to properly diagnose any problems with the continuous-use medical device. The indication provided by the flags may be displayed on the display of the continuous-use medical device or on an external display device operatively connected to the continuous-use medical device when the device is being serviced.

The circuitry 75 can be configured to store a flag in the memory (e.g., memory available to processors 1 and 2 (FIG. 5) of the continuous-use medical device. The flag can be in the form of a Yes/No (or ON/OFF) data element configured to indicate whether an underlying triggering event has occurred, e.g., based on one or more data conditions or thresholds corresponding to the parameter being monitored. For example, if the flag is set to "Yes" or "ON" an indication may be provided that a particular triggering event has occurred. On the other hand, if the flag is set to "No" or "OFF", the element indicates that conditions for a given triggering event were not met. Using the detection of an impact example provided above, the impact detector sends a signal to the circuitry 75 of the controller module 47 that the continuous-use medical device has experienced an impactor vibration event. The circuitry 75 of the controller module 47 analyzes the signal from one or more impact or vibration detector disposed in the device as described below and determines whether the detected impact is above a predetermined threshold. If the impact or vibration transgresses a predetermined threshold or has a duration that transgresses a predetermined duration level, the circuitry 75 is configured to store a flag in the memory of the continuous-use medical device. In an implementation, different flags may be used to record transgression of thresholds corresponding to an impact or a vibration. For example, a first flag may be used to record an event involving the transgression of a predetermined impact or vibration threshold level, and a second flag may be used to record an event involving transgression of a predetermined impact or vibration duration level. Similarly, separate flags may be maintained corresponding to each of the impact detection and the vibration detection events.

The flag may be configured to be retrieved and/or read from the memory of the continuous-use device when such continuous-use has ended. In one example, the use of the medical device may be deemed to be at an end when the device is sent back to the manufacturer to be serviced. In this context, the flag when retrieved from the memory, can provide an indication that the at least one triggering event, such as, but not limited to, the detection of an impact, change in temperature, or electrode fall-off, occurred. The indication may be displayed on a display device configured to allow service personnel to review such indications. This allows service personnel to have the opportunity to review various events that occurred with the device when it was in continuous use so that they can accurately and efficiently diagnose any problems with the device before returning the device to the patient or a new patient. The display device may be the display 43 of the continuous-use medical device or it may be a display external from the continuous-use medical device and operatively connected thereto. The display may provide a coding associated with the flags (e.g., a numerical, alphanumeric, color, shade, pattern, or other coding) to indicate priority, criticality, or other classification of an underlying flag. For example, such classifications may be predefined through one or more rules associated with a program stored in a memory of the continuous-use medical device or the display device employed by the service personnel to review the flag information. For example, an impact event flag may be coded red to indicate a higher criticality than, for example, an electrode fall-off event.

In another example, the circuitry 75 of the controller module 47 may be configured to classify the triggering event prior to storing the flag in the memory in response to the at least one triggering event and, based on the classification, determine whether to store the flag in the memory or initiate a self-test of the continuous-use medical device. More specifically, some triggering events may be considered minor events that most likely will not require a complete self-test of the continuous-use medical device. In such instances, rather than running a self-test on the device, the circuitry 75 will merely set a flag in memory that the triggering event occurred for later review by service personnel. Such triggering events include, but are not limited to, detection of an impact on the at least one medical device, detection of an electrode being removed from contact with the patient, and detection of a temperature in excess of a predetermined maximum temperature or less than a predetermined minimum temperature.

However, certain triggering events may adversely affect the manner in which the continuous-use medical device operates. Accordingly, the circuitry 75 of the controller module 47 may be configured to initiate a self-test if such a triggering event is detected. Such triggering events include, but are not limited to, detection of replacement of a battery of the continuous-use medical device, completion of a reset of the continuous-use medical device, and detection of delivery of at least one shock to the patient.

Triggering Events for Self-Tests

Initialization and Baselining

In one example, circuitry (e.g., including a microprocessor) in the continuous-use defibrillator can run one or more self-tests as part of an initialization process of the continuous-use defibrillator, which initialization process may occur, for example, after a software or user initiated reset of the continuous-use defibrillator.

The tests described herein may be performed in a manner and at times that do not interfere with a substantial use of the device. For example, if the device is actively performing an important task, such as charging the device capacitors, the device may suspend a scheduled test or even a reset (depending on the reset conditions) until after the task is completed (or completely cancel the test or reset).

For example, the tests can be run before or after a baselining process, e.g., a process of recording a baseline template of a patient's monitored parameters, is performed. An example baseline process is described in U.S. Pat. No. 5,944,669, which disclosure is incorporated herein in its entirety. For example, a baselining process can be initiated periodically or aperiodically in response to predetermined events, and as such, tests associated with the baseline process can follow a similar schedule.

In some examples, one or more self-tests may be based on the type of the triggering event as described in further detail below. For example, a triggering event initiated by or within a device, component, or a subsystem of the medical device may be the basis for initiating a self-test of the device, component, or subsystem. In some cases, one or more of such self-tests may also include diagnostic tests of the other devices, components, or subsystems related to the device, component, or subsystem associated with the triggering event. For example, the triggering event can be a battery event, such as battery replacement, removal, or ejection, as described below. A battery related triggering event may also be based on the battery charge level transgressed a predetermined battery level threshold. Such battery-related triggering events can cause one or more battery related self-tests to be initiated. For example, such tests can include tests of the battery voltage, high voltage converter coupled to the battery, battery power consumption tests, battery gas gauge drain tests, and tests of the internal resistance of the battery. These battery related tests can also include tests of components, devices, and/or subsystems that are directed or indirectly coupled to the battery.

In some implementations, a triggering event may be an indication that an electrode has fallen off or is causing a noisy ECG signal. Accordingly, one or more self-tests related to the ECG event can include tests of the ECG sensor circuit, sensor impedance checks, and/or electrode integrity verification tests.

Download of Patient Profile

Examples of initialization processes that could trigger a self-test comprise, without limitation, completion of the download of all or part of a patient profile or all or part of an updated patient profile into the memory of the continuous-use defibrillator accessible to the microprocessor of the continuous-use defibrillator. The patient profile or updated patient profile can comprise data unique to a patient that is to wear the defibrillator during use. This patient profile (or portion thereof) may comprise, for example, without limitation, baseline ECG signals or other criteria, such as threshold heart rate values that the microprocessor of the defibrillator utilizes to determine whether or not the patient is experiencing an arrhythmia event and, if so, to deliver a shock.

Button(s) Actuation

In another example, the microprocessor of the continuous-use defibrillator runs a self-test in response to actuation of one or more buttons (e.g., response buttons 41 of monitor 5) of the defibrillator while in use or as part of the initialization process (described above).

Periodically, aperiodically, or in response to a triggering event, the continuous-use device may carry out a test of the response buttons as follows. For example, the test may involve determining whether the actuation of the response buttons is being detected by the response button circuitry. For example, a test of the response buttons can include determining whether the one or more processors of the device is receiving an actuation signal associated with actuation of the response buttons.

Detection of Mechanical Impact or Vibration

In another example, in response to the microprocessor of the continuous-use defibrillator determining via an accelerometer or other impact or vibration detecting device, such as, without limitation, a piezoelectric device, of the continuous-use defibrillator that the continuous-use defibrillator has experienced one or more impacts or vibration in excess of a predetermined impact (amplitude) or vibration level, or a predetermined time limit stored in a memory accessible by the microprocessor, the microprocessor can set a flag and/or initiate self-testing of the continuous-use defibrillator. In another example, another impact detecting device can be an electromechanical or a mechanical switch configured to change state, e.g., from an open state or closed state, or vice versa, in response experiencing a g-force in excess of a g-force the electromechanical or mechanical switch is designed to experience without changing state. In this manner, the device can be configured to determine if any device, component, or subsystem of the medical device has been adversely affected by the impact or the vibration.

For example, the microprocessor can be programmed to be responsive to this electromechanical or mechanical switch changing state to initiate self-testing of the continuous-use defibrillator. An example of a continuous-use defibrillator that is capable of detecting impact is disclosed in U.S. patent application Ser. Nos. 14/180,775 and 14/175,433 and U.S. Pat. No. 8,676,313, each of which is hereby incorporated by reference in its entirety. The continuous-use defibrillator can also include a GPS which can be used by the microprocessor to record a GPS location where the continuous-use defibrillator experienced the impact in excess of the predetermined impact level. Examples of precision microsensors for use as electromechanical or mechanical switches for applications described herein are the SQ-SEN, ASx, and the MIN product families from SignalQuest, Inc. of Lebanon, New Hampshire.

Remotely Initiated Self-Test(s)

In another example, where the continuous-use defibrillator comprises wireless communication capabilities, such as, without limitation, cellular telephone circuitry, Wi-Fi circuitry, and/or another suitable and/or desirable wireless communication circuitry as discussed hereinabove, one or more self-tests can be triggered via the wireless communication capability.

For example, via the wireless communication capability of the continuous-use defibrillator, the continuous-use defibrillator can receive a wireless test signal which causes the microprocessor to initiate self-testing of the continuous-use defibrillator. In another example, if the wireless capability is utilized to update software or firmware of the continuous-use defibrillator, including patient profile information, the microprocessor can initiate self-testing in response to the completion of such software or firmware update. In another example, if the wireless capability can be utilized by the patient to wirelessly contact a remote support center with an inquiry or notification of an issue, the microprocessor can initiate self-testing of the continuous-use defibrillator in response to such patient initiated inquiry or notification, or in response to receiving a wireless communication (in some implementations, not necessarily a test signal) from the remote support center. In another example, the microprocessor of the continuous-use defibrillator can be programmed to periodically or occasionally wirelessly transmit the results of self-tests to the remote service center for analysis or storage. If the remote service center determines that one or more of the self-tests, either standing alone or in comparison to other self-tests that have been reported, indicate the potential for an issue with a component, subsystem, or system of the continuous-use defibrillator, the customer service center can wirelessly contact the microprocessor via the wireless capabilities of the continuous-use defibrillator to cause the microprocessor to initiate one or more self-tests and to wirelessly report the results of said one or more self-tests back to the service center via the wireless capabilities of the defibrillator. In another example, the service center can wirelessly request the microprocessor to perform one or more self-tests via the wireless capabilities of the defibrillator for any reason, e.g., as part of a periodic or occasional assessment of the operational capabilities of the defibrillator, when notifying a patient of a potential operational issue in the continuous-use defibrillator, and/or when updating the patient profile stored in a memory of the defibrillator. It should be understood to a person skilled in the art that other reasons could be contemplated and should not be limited to the ones enumerated herein.

In another example, one or more self-tests can be downloaded into the continuous-use defibrillator on or about the time it is desired to perform said one or more self-tests. In this example, it is envisioned that said one or more self-tests can be downloaded from an external device wirelessly into a memory of the continuous-use defibrillator under the control of the microprocessor of the continuous-use defibrillator without the need for patient interaction to cause said download. Also or alternatively, the user of the continuous-use defibrillator can initiate a request for one or more self-tests to be wirelessly downloaded into the continuous-use defibrillator, e.g., by pressing one or more buttons (real or virtual) on monitor 5.

Execution-Time Download Self-Test(s)

In an example, one or all of the self-tests to be run by the external defibrillator can be wirelessly downloaded into a memory of the continuous-use defibrillator accessible to the microprocessor of the continuous-use defibrillator on or about the time it is desired for said one or more self-tests to be executed. Also or alternatively, a memory of the continuous-use defibrillator can store a first subset of one or more self-tests while a second subset of one or more self-tests can be wirelessly downloaded into the continuous-use defibrillator on or about the time it is desired to execute said second subset of one or more self-tests. An advantage of storing zero or less than the full complement of self-tests to be run on the continuous-use defibrillator is a reduced requirement for memory storage to permanently store said self-tests in the memory of the continuous-use defibrillator. Another advantage is that downloaded self-tests can be tailored to account for natural or age related variances in the components, subsystems, or systems of the continuous-use defibrillator.

In an example, the results of one or more self-tests can be wirelessly communicated from the continuous-use defibrillator to a remote server or other remote storage device for storage in connection with the continuous-use defibrillator. This remote server or storage device can also store or have access to other tests performed on the continuous-use defibrillator or other self-tests run by the continuous-use defibrillator. By examining tests run on the continuous-use defibrillator or self-tests run by the continuous-use defibrillator, trends regarding the operational status or tolerances of components, subsystems, or systems of the continuous-use defibrillator can be analyzed for actual or impending failures, whereupon appropriate remedial action to address the failure or impending failure can be taken, such as, without limitation, dispatching a replacement component, subsystem, or system of the continuous-use defibrillator for replacement by the user, sending out a replacement continuous-use defibrillator, or issuing a recall alert to the continuous-use defibrillator.

It is envisioned that also or alternatively to the wireless communication capabilities of the continuous-use defibrillator, the continuous-use defibrillator can also comprise wired communication capabilities, such as, without limitation, plain old telephone service (POTS), a hard wired internet connection, a serial or parallel port, and the like for communication with a remote device. In this example, the continuous-use defibrillator includes any suitable and/or desirable communication circuitry and interfaces, such as plugs and/or receptacles, to facilitate such wired communication.

Assembly/Dis-Assembly Sensing

In another example, the continuous-use defibrillator can comprise a harness, or a garment, such as a vest or shirt, that supports the components, subsystems, or systems of the continuous-use defibrillator on a patient during use. Prior to outfitting the patient with the defibrillator, certain assembly may be needed. For example, in a continuous-use defibrillator, an electrode belt may need to be assembled within the harness or garment. For example, the electrode belt may include components such as a distribution node, therapy electrodes, and/or sensing electrodes that may be inserted within pockets in a garment. In such examples, the harness or garment can comprise sensors coupled to portions of the harness or garment that are proximate to or come in contact with the belt and/or components of the belt, and which inform a microprocessor of the continuous-use defibrillator when the belt and/or components of the belt are brought in contact with the harness or garment for assembly. In response to sensing an assembly (or disassembly) event via such sensors, e.g., insertion or removal of a therapy electrode from a pocket in the garment, the microprocessor can initiate one or more self-tests of the continuous-use defibrillator. In further examples, the device may sense the establishment of an operative connection between the electrode assembly (e.g., assembly 3) and the monitor (e.g., monitor 5) of the device. Such a connection may trigger one or more self-tests as described herein.

In an example, the harness or garment can comprise one or more snaps, buckles, or fasteners that facilitate securing the harness or garment on the patient (or securing components, systems, and/or subsystems of the device within the garment) during use and removing the continuous-use defibrillator from the patient. Each snap, buckle, or fastener can comprise a sensor, the state of which can be detected by the microprocessor, and which informs the microprocessor when the snap, buckle, or fastener is in a closed state or an open state. In response to sensing the snap, buckle, or fastener is in a closed or open state (or has transitioned to the closed or open state), the microprocessor can initiate one or more self-tests of the continuous-use defibrillator.

In one example, the snap, buckle, or fastener is a two-piece snap, buckle, or fastener wherein a first piece of the snap, buckle, or fastener has a mating arrangement that affirmatively mates with a corresponding mating arrangement of the second piece of the snap, buckle, or fastener. The first and second pieces can comprise first and second conductive segments (comprising the snap, buckle, or fastener sensor) that make contact when the two pieces are coupled together in a closed state, e.g., when the continuous-use defibrillator is being worn by a patient, which conductive segments are separated when the snap, buckle, or fastener is in an open state, e.g., when the patient is taking off or not wearing the continuous-use defibrillator. In an example, the first conductive segment can be coupled to a low voltage (e.g., 3 volt) source while the second conductive segment can be coupled in parallel to an input of the microprocessor and to ground potential via a current limiting resistor. In use, when the snap, buckle, or fastener is in the open state with the two segments not coupled, the input of the microprocessor coupled to the second conductive segment is biased to ground potential (analogous to a logical zero) via the current limiting resistor. In contrast, when the two segments are coupled together, the input of the microprocessor will detect the voltage of the low voltage source (analogous to a logical one).

Based on whether the input of the microprocessor is sensing a logical zero or a logical one, the microprocessor can determine if the snap, buckle or fastener is in an open state, or a closed state, or when transitioning between an open state and closed state, and vice versa, and can initiate self-testing upon any one or combination of these events. Other detection mechanisms can include capacitive elements, inductive elements, and/or elements that are capable of detecting changes in resistance and/or impedance values.

Round Robin Testing

In another example, the microprocessor of the continuous-use defibrillator can be programed to perform a different subset of the total number of self-tests of components, subsystems, or systems of the continuous-use defibrillator capable of being run each time a self-test cycle is initiated in some manner. For example, assume the microprocessor is programmed to run the following self-tests: (1) one or more I/O tests; (2) battery voltage test; (3) capacitor voltage test; (4) a high voltage converter output test; (5) battery power consumption test; (6) battery gas gauge test; e.g., draining faster/slower than it shows; and (7) a component test, e.g., the internal resistance of the battery.

In a first test cycle, the microprocessor can run one or more of self-tests 1-3; in a second test cycle the microprocessor can run one or more of self-tests, e.g., 4-5; and, in a third test cycle the microprocessor can run one or more of self-tests, e.g., 6-7. Alternatively, in the second test cycle, the microprocessor can run one or more of self-tests, e.g., 3-5, and in the third test cycle the microprocessor can run one or more of self-tests, e.g., 5-7 (i.e., any combination of one or more tests in any test cycle can be the same or different than any combination of one or more tests run in another test cycle).

Serialized Mismatch

In another example, various components, subsystems, or systems of the continuous-use defibrillator can be serialized in a manner that can be read by the microprocessor for comparison with serial numbers stored in a memory accessible to the microprocessor of the continuous-use defibrillator. For example, unique serial numbers may be assigned to a battery, a wireless device, etc. of the continuous-use defibrillator and these serial numbers can be stored in a memory, e.g., in the form of a database, accessible to the microprocessor of the continuous-use defibrillator, e.g., during a set-up of the continuous-use defibrillator. For example, unique serial numbers may be implemented through the use of radio-frequency identification (RFID) tags on the components. An example of the use of identification devices in a continuous-use defibrillator is disclosed in U.S. patent application Ser. No. 14/448,761, which is hereby incorporated by reference in its entirety. Thereafter, at one or more suitable times, the microprocessor can read the serial number of each component and compare it to the serial number for that component stored in the memory. In the event a read serial number does not match a serial number for the corresponding component, subsystem, or system stored in the memory, such as when a component, subsystem, or system has been replaced by a like component having a different serial number, the microprocessor can initiate self-testing. This self-testing may comprise testing of all of the components, subsystems, or systems of the continuous-use defibrillator testable by the microprocessor or a subset of these components, subsystems, or systems including the component or subsystem that the microprocessor detected as having the new serial number not stored in the memory of the continuous-use defibrillator accessible by the microprocessor.

For example, the microprocessor, upon detecting that a component or subsystem has a new serial number not stored in the memory accessible to the microprocessor, can initiate a self-test of the new component or subsystem and, upon successfully passing the self-test, the microprocessor can store the new serial number in the memory in replacement of the serial number for the component or subsystem that was replaced. If the self-test of the new component or subsystem fails, however, the microprocessor can cause a suitable indication of this failure to be output, e.g., via LEDs or a visual display of the continuous-use defibrillator, or by signaling the occurrence of the failure via wireless communication capabilities of the continuous-use defibrillator.

Current Sensing

In another example, the continuous-use defibrillator can comprise a current sensor having an output that can be read and processed by the microprocessor either directly, via an internal analog-to-digital converter (A-to-D) of the microprocessor, or indirectly, e.g., via a discreet A-to-D disposed in the signal path between the output of the current sensor and one or more inputs of the microprocessor and operating under the control of the microprocessor. More specifically, the microprocessor can cause the output of the current sensor to be sampled and can compare the sampled output to a pre-programmed value stored in a memory accessible to the microprocessor indicative of acceptable maximum (or minimum) current flow. In the event that the sampled output of the current sensor exceeds the stored pre-programmed value, suggestive of excessive (or too low) current flow, the microprocessor can initiate self-testing of one or more of the components, subsystems, or systems of the continuous-use defibrillator. In an example, the current sensor (e.g., an in-line resistor or hall-effect sensor) can be utilized by the microprocessor to monitor the current output by the batteries of the continuous-use defibrillator. Should the microprocessor determine via the current sensor that the batteries are supplying electrical current in excess (or less than) of an electrical current value stored in the memory accessible via the microprocessor, the microprocessor can initiate self-testing of one or more components, subsystems, or systems of the continuous-use defibrillator.

Temperature Sensor

In another example, the continuous-use defibrillator can comprise a temperature sensor coupled to the microprocessor, either directly or via suitable A-to-D interface circuitry. The microprocessor can sample the output of this temperature sensor to detect the ambient temperature in which the continuous-use defibrillator is operating and can compare this ambient temperature to an upper temperature value stored in a memory accessible to the microprocessor indicative of a maximum desired temperature to which the continuous-use defibrillator is designed to be exposed. In response to detecting an ambient temperature greater than the preprogrammed maximum, the microprocessor can initiate self-tests of components, subsystems, or systems of the continuous-use defibrillator. In some implementations, the memory can be programmed with a temperature value indicative of the lowest desirable temperature to which the continuous-use defibrillator is to be exposed and the microprocessor can initiate self-testing of components, subsystems, or systems of the continuous-use defibrillator if, via the temperature sensor, the microprocessor determines that the ambient temperature is below this lower temperature value stored in the memory. In an example, the microprocessor can also be programmed to sense for a temperature change outside of predetermined limits or exposure to a rate of temperature change outside of predetermined limits.

Moisture Sensor

In another example, the continuous-use defibrillator can comprise a moisture sensor that is coupled directly or via suitable interface circuitry to the microprocessor. For example, the continuous-use defibrillator can be rated according to an industry standard code, such as, the International Protecting Rating (IP rating). A moisture sensor can detect conditions and or events that are implicated, for example, by the IP rating of the device. For instance, the moisture sensor can be configured to detect vertically dripping water and either provide an alert or take corrective action (e.g., events that implicate an IP22 rating). In some cases, the sensor can be configured to detect and respond to water falling as a spray at a range of angles (e.g., up to 60°) from the vertical, splashing from any direction against an enclosure of the device, projections from a nozzle against the enclosure, water ingress, and/or immersion.

In an example, the moisture sensor can comprise a pair of conductors held in spaced relation by or on a substrate. In the absence of moisture or water bridging the gap between the spaced conductors, no electrical current will flow between the conductors in response a voltage applied between the pair of spaced conductors. In contrast, in response to moisture bridging the gap between the spaced conductors, an electrical current will flow between the spaced conductors. The microprocessor can be programmed to initiate self-testing in response to detecting electrical current flow across the spaced conductors.

In some implementations, the microprocessor can be programmed to not initiate self-testing based on the absence of current flow across the spaced conductors indicative of the absence of water or moisture bridging the spaced conductors. In order to detect current flow across the spaced conductors, the moisture sensor can be coupled between an input of the microprocessor and a suitable low voltage source. This input can be one that the microprocessor periodically or aperiodically samples or can be an interrupt input of the microprocessor which, in response to detecting current flow across the spaced conductors, triggers an interrupt handling routine of the microprocessor that initiates self-testing of components, subsystems, or systems of the continuous-use defibrillator to determine if the exposure to moisture is having any effect on the operation of one or more of said components, subsystems, or systems of the defibrillator.

Remaining Battery Power

In another example, the microprocessor can be programmed to initiate self-testing based upon the remaining electrical power stored in the battery of the continuous-use defibrillator. For example, upon detecting via an A-to-D, that the available power is at, for example, without limitation, 90% of the maximum available power in the battery, the microprocessor can initiate self-testing of components, subsystems, or systems of the continuous-use defibrillator. It is envisioned that one or more other percentages of the power available in the battery may be utilized as a basis for initiating such self-tests.

Critical Error Handling

In another example, in response to the microprocessor receiving notification of a potentially critical error of a component, subsystem, or system of the continuous-use defibrillator, the microprocessor can be programmed to disable and/or initiate a self-test of the component, subsystem, or system experiencing the potentially critical failure. In some implementations, the microprocessor can cause a suitable warning to generate an alert to the patient and/or the service center of the potentially critical failure. The patient alert can be a tone output by a speaker, one or more lamps or LEDs of the continuous-use defibrillator flashing, and/or the display of a warning message on a display of the continuous-use defibrillator. The warning to the service center may be via a wired or wireless connection described above. For example, in response to the microprocessor determining a failure of a self-test of a component, subsystem, or system of the continuous-use defibrillator, the microprocessor can be programmed to take appropriate remedial measures. In another example, in response to detecting a capacitor voltage input failure (e.g., of a capacitor of capacitor bank 67), the microprocessor can be programmed to learn the charge time of the capacitor and then charge the capacitor via time measurement instead of reading capacitor voltage directly.

Upon the service center being notified of a failure of a component, subsystem, or system of the continuous-use defibrillator, or the entire continuous-use defibrillator, either via the microprocessor automatically notifying the service center via a wired or wireless connection, or via the user notifying the service center, the service center can record the occurrence of this failure and automatically initiate a process of sending the patient a replacement component, subsystem, system or continuous-use defibrillator, as the case may be. For example, if a self-test determines that a battery is out of tolerance, the service center being informed of this fact, can automatically initiate sending the patient a replacement battery.

Batter, Replacement

Some of the self-tests described herein can be launched (manually or automatically) when a battery is removed, replaced, or otherwise ejected. For example, the battery chamber may comprise a sensor that detects when a battery is either removed or inserted into the device and causes the device to initiate a selected series of self-tests. In some examples, the sensor may indicate when a battery may have fallen out or otherwise ejected from the battery chamber. For example, in a continuous-use defibrillator, a patient or a caregiver can replace the defibrillator's batteries every day. In such cases, certain critical self-tests can be performed immediately after the batteries are replaced. For example, battery related tests for checking an output voltage and current threshold of the battery can be performed immediately and whenever a battery is inserted into the battery chamber. In some examples, certain self-tests described herein can be launched when a battery is replaced, but may be configured to be executed at different intervals, e.g., every $2^{nd}$ or $3^{rd}$ time a battery removal/insertion event is detected. In some examples, if a critical self-test fails, then additional self-tests described herein may be initiated. In some examples, a patient may manually cause the device to perform one or more additional self-tests after insertion of the battery.

As noted above, some of the tests described herein can be performed daily, weekly, monthly, upon initialization of the continuous-use defibrillator, e.g., after installing new patient parameters in a memory accessible to the microprocessor, in response to detecting an event, such as the buckle sensor transitioning from an open state to a closed state or vice versa, the moisture sensor detecting moisture, the microprocessor detecting a new serial number of a component, subsystem, or system of the continuous-use defibrillator, the microprocessor detecting via the accelerometer an impact in excess of a predetermined impact level, the receipt of a wired or wireless test signal from an external source, the detection, via a current sensor, of a current in excess of (or less than) a preprogrammed current, a temperature greater than or less than a preprogrammed maximum or minimum temperature, the value of the gas gauge, and the like.

Where a continuous-use medical device, e.g., a continuous-use defibrillator, includes multiple microprocessors, the detection of one or more events and the launching of one or more self-tests can be under the control of one or more of the microprocessors. In another example, a continuous-use medical device can be configured whereupon a first microprocessor has primary responsibility for detecting one or more events and launching of one or more self-tests, while a second microprocessor can be configured to detect the one or more events and launch the one or more self-tests in the event the first microprocessor does not timely launch the one or more self-tests in response to the occurrence of the one or more events, e.g., the first microprocessor is not detecting the one or more events or is not responding to the one or more events. In another example, a first microprocessor and a second microprocessor of the continuous-use medical device can be configured to perform a first subset and a second, different subset, respectively, of the available self-tests that can be performed.

Countdown Timer

In an example, the continuous-use defibrillator can include a countdown timer (CDT) (not necessarily the WDT mentioned above) having an output that can be sensed by the microprocessor and which can, optionally, be reset via the microprocessor. The duration of the countdown period of the CDT can be selected in any suitable and/or desirable manner by one skilled in the art. The countdown period can be on the order of seconds, minutes, days, weeks, months, or years. The microprocessor can be configured to be responsive to the expiration of the countdown period for initiating one or more self-tests. Optionally, the microprocessor can be operative for resetting the countdown period to a starting value after expiration of a previous countdown period. In another example, also or alternatively to the CDT, the continuous-use defibrillator can include a time/date clock that the microprocessor can sample at different times, compare a difference between two times/dates to a predetermined value stored in the memory, and can initiate one or more self-tests when the difference exceeds the predetermined value.

Multi-Tasking

In an example, the microprocessor can multi-task, with part of the microprocessor's processing time dedicated to patient monitoring and/or treatment and with another part of the microprocessor's processing time dedicated to performing one or more self-tests. In this example, it is envisioned that the processing time dedicated to patient monitoring does not compromise the microprocessor's monitoring and/or treatment of the patient.

User Activity

In an example, the microprocessor can determine patient activity, e.g., via an activity sensor, such as an accelerometer, and can decide based on said determined activity whether or not to perform one or more self-tests. In one example, in response to the microprocessor determining that the patient is active and moving about, indicative of the absence of a life-threating cardiac event, the microprocessor can perform one or more self-tests. In another example, in response to the microprocessor determining that the patient is stationary and that the patient's ECG signals are normal, the microprocessor can perform one or more self-tests. Further, one or more user actions may be the basis of a self-test initiated by the device. For example, a patient may manually select one or more self-tests as described herein to cause the device to initiate the selected self-test. For instance, if the patient wishes to test the charge holding capacity, charging circuitry, and/or converter circuitry in connection with a readiness test, the patient may initiate a corresponding self-test of the relevant portion(s) and/or component(s) of the medical device. For instance, the patient may use the user interface to browse to a screen displaying a list of diagnostic device tests that the patient may select, e.g., by touching a touch-sensitive display, a soft or physical button, providing a voice command, or other input. For example, the patient may be authorized to cause only a subset of available self-tests to be executed on the device. In some implementations, the patient may be remotely authorized via a remote wireless signal from a remote server to access one or more self-tests. In such cases, a remote technician may enable access to one or more self-tests via the remote server. The patient may then interact with the medical device to cause the test(s) to execute and review the results. The results of such tests may also be transmitted to the remote server and displayed to the remote technician via a workstation operatively coupled to the remote server.

Post Shock Delivery

In an example, the microprocessor can initiate one or more self-tests after administering one or more shocks to the patient.

Upload or Download of Data

In an example, the microprocessor can initiate one or more self-tests in response to the uploading of data into a memory or an RFID tag (discussed hereinafter) of the continuously on medical device or the downloading data from the memory or the RFID tag of the continuously on medical device, e.g., without limitation, via communication module 49 or directly into or out from the RFID tag. The data can include software and/or firmware. The data can also or alternatively include parameters, constants, and/or variables used in connection with software and/or firmware. In an example, the microprocessor can set a flag in memory when uploading or downloading data. At a suitable time, in response to this flag being set, the microprocessor can initiate one or more self-tests.

Excessive Strain Detection

In an example, the continuous-use defibrillator can include one or more strain gauges operatively coupled to the microprocessor for enabling the microprocessor to detect when one or more components, subsystems, or systems of the continuous-use defibrillator has experienced strain in excess of a predetermined level of strain. For example, without limitation, the PCB supporting one or more of controller module 47, communication module 49, energy storage module 44, and/or discharge module 42 can include thereon a strain gauge that is operatively coupled to enable the microprocessor to detect the output of the strain gauge.

In some examples, cabling used to connect one or more components (e.g., in an electrode belt assembly, one or more cables are used to connect the various therapy electrodes, and/or sensing electrodes, and/or distribution node) can be subject to one or more tensile forces during use. For example, the cabling may be qualified according to tensile strength tests specified in, for example, IEC 60601-24:2010, Clause 201.15.4.101b Test1, and IEC 60601-1:2005, Clause 8.11.3.5. For example, the cabling may be required to sustain up to 25 cable pulls at a pull force of 25 lbs, and have cable jacket displacement of less than 2 mm. Further, the cable tensile pull to failure requirement can be about 50 lbs. minimum tensile strength. In some cases, the minimum tensile strength can be set to withstand at least 75 lbs. Accordingly, sensors can be placed, e.g., near or proximate to cable anchor point(s) (e.g., tie-off points or strain clamps), or along the cable to detect cable and/or anchor point(s) forces in excess of one or mom predetermined tensile strength values. For example, if the tensile force comes within 25% of a minimum tensile force, the monitor 5 can issue an alert to the patient. Further, the monitor can immediately initiate a series of self-tests to verify the integrity of the components of the device in accordance with the principles described herein.

In an example, the strain gauge can be a piezoelectric transducer that is coupled to the microprocessor via a D-to-A or a simpler circuit, such as an electronic latch that compares the output of the strain gauge to a preset voltage level and switches the level and output between a logical 0, a logical 1, or vice versa, in response to the voltage output by the strain gauge exceeding the reference voltage, for example. In response to the microprocessor detecting that the strain gauge has output a voltage indicative of detecting strain in excess of a predetermined level of strain, the microprocessor can initiate one or mom self-tests.

Tampering

In an example, a self-testing circuit (e.g., coupled to a microprocessor) can initiate one or more self-tests in response to detecting tampering or attempted tampering of one or more components, subsystems, or systems of the continuous-use defibrillator. For example, to effect tampering detection, housing 31 of monitor 5 can include at least two housing sections joined to form the housing 31 (e.g., a two-piece housing), and further include a tampering detection element as the monitoring component. For example, such a tampering detection element can include a breakaway conductor 74 (shown in phantom in FIG. 2) that extends between the two housing sections. In some examples, the tampering detection element can include circuitry that is responsive to the breakaway conductor 74 becoming an open circuit (i.e., the breakaway conductor breaks open) or becoming detached from one or both housing sections. Based on detecting the open circuit, the tampering detection element can trigger one or more self-tests to be performed by the self-testing circuit. In an example, the self-testing circuit can be implemented by a microprocessor.

Accordingly, the tampering detection element can include the breakaway conductor 74 such that one end of breakaway conductor 74 can be coupled in parallel with an input of the microprocessor and a reference potential (e.g., ground) via a biasing resistor. The other end of breakaway conductor 74 can be coupled to a voltage source. With the two housing sections joined to form housing 31, the input of the microprocessor detects the voltage of the voltage source impressed across the biasing resistor via breakaway conductor 74 (analogous to a logical 1). When the two housing sections are opened, whereupon breakaway conductor 74 becomes open or becomes detached from one or both housing sections, the voltage source becomes isolated from the input of the microprocessor and the input of the microprocessor is biased to the reference potential (analogous to a logical 0) via the biasing resistor. In response to detecting the change from the logical 1 to the logical 0, the microprocessor initiates one or more self-tests.

For example, self-tests can include performing one or more microprocessor self-tests, battery capacity tests, battery status, remaining run time, RAM/ROM tests, among others, and writing one or more states and/or results of these tests to a nonvolatile memory for later retrieval. For example, the monitor 5 can also display a warning message to the user in connection with the tampering and/or attempted tampering. In some examples, the capacitor charge capacity can be checked through one or more capacitor tests described below, and if a significant charge is retained by the capacitor, a warning alarm sequence can be initiated to warn the user of the potential for an electric shock.

Another example tampering detection that can cause a controller (e.g., programmable logic devices and arrays, application specific integrated circuits, hardware and software combinations, general purpose processors and dedicated controllers) to display a notification that components of a treatment device have been tampered with or damaged is disclosed in U.S. Pat. No. 8,649,861, which is incorporated herein by reference.

For example, the treatment device (e.g., the wearable defibrillator 1) can include one or more activity sensors, such as accelerometers. For example, a first accelerometer can be located on or within distribution node 11 and a second accelerometer can be located on monitor 5. In one embodiment, the first accelerometer is positioned on the subject's upper body, and the second accelerometer is positioned proximate to the subject's waist. Accelerometers or other activity sensors may also be positioned on the subject's limbs. Activity sensors, including accelerometers, may include at least one position, force, or motion detector. In one embodiment, a monitoring element can use information detected by multiple activity sensors, such as the accelerometers to determine and predict subject activity, and to calibrate or verify the accuracy of one or more sensors (e.g., electrode sensors and/or acoustic sensors). For example, one or more of electrode or acoustic sensors tasked with determining the subject's heart beat may shift due to movement or be improperly positioned so that an inaccurate (e.g., reduced) heartbeat is reported. In this example, activity sensors may indicate that the subject is exercising and where an elevated heartbeat would be expected, while the sensors detect a reduced heart beat or no heart beat because it is improperly positioned on the subject. A controller can identify this discrepancy and notify the subject, for example by a display on monitor 5, that one of the sensors should be repositioned. Further, based on this discrepancy identified as a triggering event, the self-test circuit can initiate a series of self-tests, e.g., to verify the integrity of the sensing elements. By processing sensed information and information received from the user, the self-test circuit may determine that one or mom components, subsystems, or systems of the continuous-use defibrillator may have been tampered with or damaged, and the monitor 5 can display a notification of any such tampering or damage.

Any one or combination of the above or following self-tests can be run in response to the insertion or removal of the battery, on a monthly schedule, on a weekly schedule, on a daily schedule, or continually.

Self-Tests Performed by the Medical Device

Example Self-Test(s)

Examples of self-tests that can be run by self-testing components (e.g., circuitry or microprocessors) comprise, without limitation, one or more of the following tests: battery capacity; remaining battery run time; battery status; status of user response buttons; determining if ECG monitoring signal quality is compromised by noise or electrode fall-off; ECG signal intensity, confirming detection algorithm parameters, therapy electrode placement and impedance levels; and operation of various electrical components, subsystems, or systems of the continuous-use defibrillator, for example, a DC-DC converter of the defibrillator. More specifically, self-tests that can be performed by the microprocessor can comprise, without limitation, background checks of inputs and outputs (I/O); tests of the battery voltage, capacitor voltage, and a high voltage converter, system-wide tests, such as testing battery power consumption, battery gas gauge draining faster/slower than it shows, one or more individual component checks, like internal resistance of the battery, and the like. Finally, tests can comprise looking at values of individual parts. Any combination of one or more self-tests can be initiated by the microprocessor periodically, aperiodically, randomly, in response to receiving an appropriate signal at an input of the microprocessor, in response to the microprocessor sampling at an input (analog and/or digital input) a condition of a component, subsystem, or system that the microprocessor is programmed to trigger a self-test in response to, or some combination thereof. Unless otherwise specified, the particular manner in which the self-testing component initiates one or more self-tests is not to be construed as limiting the disclosure.

Microprocessor Self-Test

The microprocessor self-test is a functional test wherein the one or more microprocessors within the medical device can test the integrity of its internal registers and verify its access to local and external memory. Upon detecting a failure, the microprocessor can attempt to notify the user of the system failure.

Gate Array

A system gate array self-test enables the microprocessor to verify that it can write to and read from system gate array registers. This test can incidentally test other components, subsystems, or systems of the continuous-use defibrillator.

System Monitor

System monitor 5 self-test verifies that the microprocessor can write to and read from the system monitor.

CRC Test

A cyclical redundancy check (CRC) self-test is run on read only memory (ROM) of the continuous-use defibrillator to determine the functionality of said ROM.

RAM Tests

A RAM or checksum self-test writes a pattern to system RAM and then calculates a checksum based on the system RAM contents. This checksum test can verify address and/or data faults within the RAM. A video RAM checksum self-test can be similarly utilized to verify whether video RAM is experiencing address and/or data faults. A device/RAM checksum test can determine if a flash RAM is experiencing an address and/or data fault.

Watchdog Timer (WDT)

A system watchdog verify self-test can verify if a watchdog timer detectable by a microprocessor is working properly. For example, where the watchdog timer is coupled to an interrupt input of a microprocessor, the microprocessor can temporarily disable its interrupt input connected to the output of the watchdog timer and then issue a reset command to the watchdog timer. Thereafter, the microprocessor can monitor the time between when it outputs the watchdog reset signal and the time the disabled interrupt input of the microprocessor changes state indicative of the expiration of the watchdog timer. Based on this test, the microprocessor can confirm that the watchdog timer is indeed functioning and outputting an appropriate expire signal within an appropriate time interval. In the event the watchdog timer either does not output the expire signal or outputs the expire signal after a predetermined time interval programmed into the memory of the microprocessor, the microprocessor can signal this as a failure of the watchdog timer.

Removable Memory Card

If the continuous-use defibrillator is provided with a removable memory card, a card self-test can be provided to check for the presence and type of removable memory card, and, optionally, a CRC or a RAM test mentioned above.

Electrode

For example, self-tests as described herein can be initiated when one or more sensing and/or therapy electrodes are deemed as not making sufficient contact with the patient. For example, an electrode may fall off the patient, or be disengaged from the patient during a patient activity. Such electrode events may be based on, for example, determining a patient impedance as seen by the electrode. For instance, if the patient impedance exceeds a predetermined value, the device may set a flag indicating electrode fall-off. Further, ECG self-tests can confirm that the patient electrodes of the continuous-use defibrillator when in use are properly receiving ECG signals from the patient and that an ECG electrode has not fallen off. For example, a noisy ECG signal or an ECG signal that is prone to excessive variations may be a basis for declaring an ECG fall off event and setting a corresponding flag. In some implementations, to determine whether an ECG electrode has fallen off, a low amplitude 800 Hz signal is presented to a first ECG electrode that is physically touching the patient's body. By sampling for this 800 Hz signal at a second ECG electrode that is physically touching the patient's body, the microprocessor can determine that the first and second ECG electrodes are indeed in contact with the patient's body. The process of using one electrode to apply the low amplitude 800 Hz signal and a second electrode to detect the presence of the 800 Hz signal can be repeated for each possible pair of electrodes provided for ECG monitoring. In an implementation, the monitoring component as implemented by a processor (e.g., processor 69) or circuitry 75 can execute a state machine for carrying out ECG electrode fall off tests. In this regard, the monitoring component can effect a change in a corresponding flag in memory on detecting the ECG fall off event.

In an implementation, the monitoring component as implemented by a processor (e.g., processor 69) or circuitry 75 can execute a state machine for carrying out therapy electrode fall off tests. For example, the processor or circuitry can detect an underlying parameter (e.g., voltage drop indicative of a resistance of a path from the therapy electrode to the patient's skin) that falls outside a predetermined range. If the voltage being measured is outside the predetermined range, then a therapy electrode fall off state is indicated. In response, the monitoring component can effect a change in a corresponding flag in memory on detecting the therapy electrode fall off event.

Battery

Battery self-tests can also be run. For example, certain self-tests described herein (including the battery self-tests) may be initiated upon detecting when a battery charge level transgresses a predetermined battery charge threshold (e.g., 10% of full battery charge capacity). Different tests may be initiated at different battery charge levels. For instance, when the battery charge is at or below a critical charge level (e.g., 10%) the device may initiate a first set of self-tests that are different when the battery charge level falls below another predetermined threshold (e.g., 25%). One battery test can be the remaining battery power test mentioned above whereupon the microprocessor can initiate self-testing upon detecting that the available power or voltage is at some predetermined percentage of the maximum available power or voltage in the battery. Another battery test can be a battery load test where a no-load voltage of the battery ($V_{NL}$) is measured and, separately, the output of the battery is connected to a load resistor and the voltage of the battery connected to a load ($V_L$) and the current ($I_L$) output by the battery to the load resistor are measured. The internal battery resistance ($R_i$) is then determined from the formula: $R_i = (V_{NL} - V_L)/I_L$, or an equivalent formula. If the microprocessor determines that the internal battery resistance current falls outside of an acceptable limit, this can be deemed by the microprocessor to be indicative of battery failure or an impending battery failure.

Battery Charging

Another test is a test of the ability of the charger to charge the battery. This test can involve the microprocessor monitoring the battery voltage during charging of the battery between a first voltage or percentage of full charge and a second voltage or percentage of full charge and comparing this time to an acceptable time or range of times for charging the battery between these two voltages or percentages. If the actual time to charge the battery is outside of the acceptable time or range, the microprocessor can signal this as a potential problem with the charger or the battery. One or more separate battery tests can be performed to determine whether the battery is operating properly, whereupon if the battery is determined to be operating properly, the microprocessor can be programmed to output an indication that the battery charging circuitry is not operating properly.

Power Converter Test

The continuous-use defibrillator can comprise a high voltage power converter operating under the control of the microprocessor for charging capacitor bank 67 which stores the energy utilized to deliver a shock to the patient at an appropriate time. In an example, capacitor bank 67 comprises four parallel connected 650 µf capacitors each of which has a 390 volt surge rating and which are charged by the high voltage power converter in approximately 20 to 25 seconds from a fully charged battery. Electrical current through the four parallel connected capacitors is limited by a charge resistor in series with a switch connected to the parallel connected capacitors. When it is desired to charge the capacitors, control signals from the microprocessor turn on the high voltage power converter and close the switch in series with the charge resistor. Under the control of the microprocessor, an A-to-D can measure and compare the output voltage of the high voltage power converter during charging of the capacitor bank to a predetermined voltage or range to verify operational integrity. For example, if the output voltage is substantially the same as the predetermined voltage or substantially falls within the predetermined voltage range, the power converter may be deemed to be operating as expected. For example, the results of the power converter test may be written to one or more registers in the memory of the continuous-use defibrillator, e.g., for later review by technicians. If the output voltage is not substantially the same as the predetermined voltage or substantially falls outside the predetermined range, one or more flags may be set in the memory of the continuous-use defibrillator for review. If desired, the current supplied by the high voltage converter during charging of the capacitor bank can also be measured and compared via a current sensor connected to a different A-to-D or the same A-to-D that was utilized to measure the voltage output by the high voltage converter, e.g., via a multiplexer also under the control of the microprocessor. The current output by the high voltage power converter during charging of the capacitor bank can be completed to a predetermined current value or predetermined current range similar to the voltage measurements described above.

Capacitor Charge Retention Test

A particular self-test can comprise measuring the ability of the capacitor bank 67 to maintain a charge over a period of time. For example, the microprocessor, via an A-to-D, can measure the voltage of the capacitor bank 67 initially after charging and thereafter, on a periodic or random basis, can measure the voltage of the capacitor bank 67. Based on the change in voltage from the initially charged voltage over time, the microprocessor can determine if the capacitor bank is able to maintain a predetermined level of charge over a predetermined period of time. Also, if the microprocessor determines that the charge in the capacitor bank 67 has dropped to an unacceptable level, the microprocessor can cause the capacitor bank to be charged from the high voltage power converter in the manner discussed above.

Capacitor Charge/Discharge Test

Also or alternatively, the capacitor bank of parallel connected capacitors can comprise in parallel therewith a discharge resistor and a switch that operates under the control of the microprocessor. Herein, a "switch" can be a mechanical switch or a suitable semiconductor transistor. The discharge resistor can be utilized to safely discharge the capacitor bank without having to actually shock a patient. In an example, under the control of the microprocessor, the capacitor bank can be alternately charged and discharged via the charging resistor and the discharge resistor and the voltage and current during said charging and discharging can be measured to determine whether the capacitor bank is operating to predetermined criteria, e.g., charging to full capacity within a certain interval of time or range of time, discharging from a starting voltage level to a predetermined lower voltage level within a predetermined period of time or range of times, and the like.

In some implementations, the capacitor banks can be periodically charged (e.g., through the converter) and discharged (e.g., through a bank of discharge resistors as described below) to verify an integrity of the battery and capacitor charge circuitry, (e.g., once or twice every week according to a preset frequency and/or time parameter stored in memory)

Patient Discharge Resistor

In an example, the continuous-use defibrillator can be equipped with another test load resistor to simulate the resistance of a patient connected between of the capacitor bank, with the capacitors connected in series instead of parallel for charging purposes. By way of this test load resistor, a self-test of the discharge capabilities of the capacitor bank to a simulated patient can be performed. In the case where the continuous-use defibrillator applies a biphasic waveform to a patient, four transistors (GBTs) arranged in an H-bridge configuration can be utilized to deliver the two phases to the resistor acting in the capacity as a simulated patient. By way of this test, the microprocessor can determine if the transistors of the H-bridge are properly operating by monitoring the voltage and/or current during discharge of the capacitor bank through the test load resistance in both directions. The test load resistance (utilized to simulate a patient) can be connected in parallel with the patient when the continuous-use defibrillator is in use. A switch can be used to alternately conned the test load resistance and the patient to the output of the capacitor bank during testing and in normal use. During testing, the switch connects the test load resistor to the output of the capacitor bank via the H-bridge configuration and, by controlling the transistors on each leg of the H-bridge configuration, discharges the capacitor bank through the test load resistor. For the purpose of testing the switching capabilities of the transistors of the H-bridge configuration, the test load resistor does not necessarily have to have the same resistance as a simulated patient. Rather, the test load resistor can have any resistance deemed suitable and/or desirable for testing the switching capabilities of the transistors of the H-bridge configuration. For example, whereas a typical patient may have a resistance of 50 ohms, the test load resistor can have a resistance of, for example, without limitation, 200 ohms or greater. Based on the discharge time of the capacitor bank determined in a manner known in the art based on the product of the capacitor value and the test load resistor the microprocessor can calculate the value of the test load resistor and the capacitance of the capacitor bank. If the value of either the test load resistor or the capacitance of the capacitor bank varies by more than a predetermined amount, this can be indicated as a failed self-test.

Shock Discharge

In another example, if the current being supplied to a patient during delivery of a shock falls below a normal level, this condition is indicative of one of the electrodes having become detached from the patient.

Integrity Check of Cell or Bladder of One or More Therapy Electrode Pads

Each therapy electrode pad includes one or more conductive gel reservoirs, a.k.a., cells or bladders, each of which has a gel delivery outlet, wherein the gel reservoir is fluidly coupled to a fluid pressure source. The fluid pressure source can be a source of any suitable and/or desirable fluid pressure, such as, without limitation, an air pump, a pressurized gas cylinder, and the like. A fluid channel can connect the fluid pressure source to each conductive gel reservoir. A suitable pressure gauge, such as a piezoelectric transducer or a gas pressure controlled switch can be coupled to measure the pressure in the fluid channel and to provide an output that can be sampled by the microprocessor, either directly or via a D-to-A. In use, under the control of the microprocessor, fluid from the fluid pressure source can be selectively introduced into the conductive gel reservoir to a pressure level less than needed to open the gel delivery outlet of the gel reservoir. Thereafter, via the fluid pressure gauge, the microprocessor can verify that the pressure applied to the conductive gel reservoir is maintained at or above a predetermined pressure for a predetermined interval of time.

For example, assume that the gel delivery outlet is configured to pass conductive gel when the pressure applied to the conductive gel reservoir is greater than or equal to 10 psig. For the purpose of testing the fluid integrity thereof, the conductive gel reservoir can be exposed to a fluid pressure of, for example, 7 psig. Thereafter, the microprocessor can monitor the time it takes for the pressure to fall from 7 psig to, for example, 5 psig (due to natural leakage of pressure from the conductive gel reservoir) and can compare this time to a time that is indicative of acceptable fluid integrity of the conductive gel reservoir (and the fluid conduit) to maintain a suitable level of fluid pressure. Details regarding therapy electrodes including conductive gel reservoirs can be found in U.S. Pat. Nos. 8,880,196 and 5,078,134, the contents of both of which are incorporated herein by reference.

Electrode/Therapy Pad Placement Sensing

In an example, the placement of one or more electrodes 7a, 7b, 7c, 7d and/or one or more therapy pads 13a, 13b, 13c at appropriate locations of garment 2 can be sensed by the microprocessor. In response to detecting proper or improper placement of one or more electrodes or therapy pads, the microprocessor can output a suitable audio and/or visual indication on monitor 5.

For example, without limitation, each electrode 7a, 7b, 7c, 7d can be positioned at a suitable location on garment 2 via a suitable fastener that includes two or more pieces that can be separated and joined to form an open or closed electrical circuit that can be sensed by the microprocessor. In one example, one piece of the fastener can be connected to a low-voltage, current-limited source of electrical power while the other piece of the fastener can be connected in a manner for detection by the microprocessor. For example, the other piece of the fastener can be connected in parallel to an input of the microprocessor and to an electrical ground via a current limiting resistor. In this example, when the two pieces of the fastener are not connected, whereupon the circuit formed by the fastener is open, the input of the microprocessor will be at ground level via the current limiting resistor (analogous to a logical 0). In contrast, if the two pieces of the fastener are in a closed or connected state, whereupon the circuit formed by the fastener is closed, voltage from the low voltage source can be impressed on the current limiting resistor via the closed fastener and the microprocessor can detect this voltage on the current limiting resistor (which voltage is analogous to a logical 1).

In an example, each of the therapy pads 13a, 13b, 13c can be received in a pocket of garment 2 wherein said pocket holds said therapy pad 13a, 13b, 13c in a desired position and in suitable pressure contact with a patient when the garment 2 is worn by the patient. Each pocket can include a fastener having a first part connected to a low voltage source and having a second, mating part, connected in parallel to ground potential via a current limiting resistor and to an input of the microprocessor, either directly or via interface circuitry. In a manner similar to the fastener discussed above in connection with electrodes 7a, 7b, 7c, 7d, when the fastener associated with therapy pads 13a, 13b, 13c is in an open state, the microprocessor senses the reference ground (analogous to a logical 0). In contrast, when the fastener is associated with the therapy pad is closed, the voltage from the low voltage source is impressed across the current limiting resistor and the microprocessor senses this voltage across the current limiting resistor (analogous to a logical 1).

While the use of fasteners on garment 2 has been described, it is also envisioned that other means can be used for detecting the appropriate positions of one or mom electrodes and/or one or more therapy pads within garment 2 when worn by a patient. For example, a side of an electrode 7a, 7b, 7c, 7d or therapy pad 13a, 13b, 13c in contact with the harness, shirt, or other apparel forming garment 2 can include a conductive surface that, when appropriately positioned, creates an electrical continuity between a pair of spaced conductors of the harness, shirt, or other apparel. This continuity (or lack thereof) can be sensed by the microprocessor in any suitable and/or desirable manner selected by one of ordinary skill in the art. In response to detecting continuity, the microprocessor interprets this as meaning that the electrode 7a, 7b, 7c, 7d or therapy pad 13a, 13b, 13c is appropriately positioned. In contrast, in the absence of such continuity, the microprocessor can interpret this as the electrode or therapy pad being out of position.

In response to determining that an electrode or therapy pad is or is not properly positioned in garment 2 and in suitable contact with the patient, the microprocessor can output a suitable audio and/or visual indication of this via monitor 5.

User Interface Test

In an example, in response to the microprocessor causing monitor 5 to output one or more predetermined visual images on display screen 43, and/or causing one or more predetermined audio tones output by a speaker port, and/or causing one or more predetermined lamps or LEDS of monitor 5 to illuminate, the user can be prompted via an audio or visual prompt to press one or more of the buttons of monitor 5 if the predetermined image is displayed on display screen 43, if the predetermined audio output is output by the speaker port, and/or if the one or more predetermined lamps and/or EDS are on thereby enabling the user to confirm to the microprocessor the operational status of the display screen, the speaker port, and/or the lamps or LEDs.

In an example, the microprocessor can cause a predetermined image to be displayed on display screen 43 and can request a patient via the speaker to confirm that the predetermined image is, in-fact, being displayed by pressing a first button or by confirming that the predetermined image is not being displayed by pressing a second button. In another example, the microprocessor can cause the speaker port to output one or more messages requesting the user to press one or more buttons of monitor 5. The buttons can be mechanical buttons and/or virtual buttons displayed on display screen 43.

In another example, microprocessor can request the user to press one or more buttons in response to the operation of tactile simulator 12. The request to the user to press the one or more buttons can be made via a visual display on display screen 43 and/or via one or mom messages output by a speaker port.

Communications Capabilities

In an example, one or more self-tests can include periodic, aperiodic, or on-demand tests (e.g., based on a triggering event) of the device communication capabilities, e.g., via the communications module. In some examples, such tests can include establishing a link to a base station and sending a wireless test signal. Both receiving and transmitting capabilities can be tested through such a process. If the signals are received on one or both ends, appropriate flags can be written to the memory indicating the status of the communications capability. A similar process can be implemented for testing communications with a remote server.

Finally, it is envisioned that one or any combination of the foregoing conditions that trigger self-tests, any one or combination of self-tests, and any one of mom combination of the output of the self-tests can be implemented by the microprocessor of the continuous-use defibrillator.

Output of Self-Test Results

The results of one or more of the self-tests discussed hereinabove can be displayed on a display of the continuous-use defibrillator and/or communicated to another device, such as a central processor or to a second device, such as a smart phone, or tablet computer, which may be used as a diagnostic tool. Such displayed output may comprise the results of one or more individual self-tests or a global indication, e.g., "self-tests pass" or "self-tests fail" and may comprise instructions, such as "Notify the Manufacturer." If the continuous-use defibrillator comprises wireless communication capabilities, the results of self-tests can be wirelessly communicated to a service center for storage and/or analysis. This wireless communication can also comprise the identity and/or serial number of the continuous-use defibrillator, and/or a geographical location of the continuous-use defibrillator determined in any suitable or desirable manner, such as, without limitation, via a GPS chip of the continuous-use defibrillator, a geographical location determined via a Wi-Fi address that the continuous-use defibrillator utilizes to communicate the test results to the service center, and the like.

In another example, the continuous-use defibrillator can comprise an RFID tag that can be read by and/or written to by the microprocessor. In this example, test results can be stored in the RFID tag which can be read by a separate RFID reader, e.g., when the continuous-use defibrillator is returned for service and/or refurbishment.

In another example, the continuous-use defibrillator can be configured so that the microprocessor can be coupled into wired and/or wireless communication with a remote user interface which can be operative for displaying individual self-test results and/or a global indication of the status of the external defibrillator, e.g., "self-tests pass" or "self-tests fail".

Example Self-Test Flow

Figure 7:
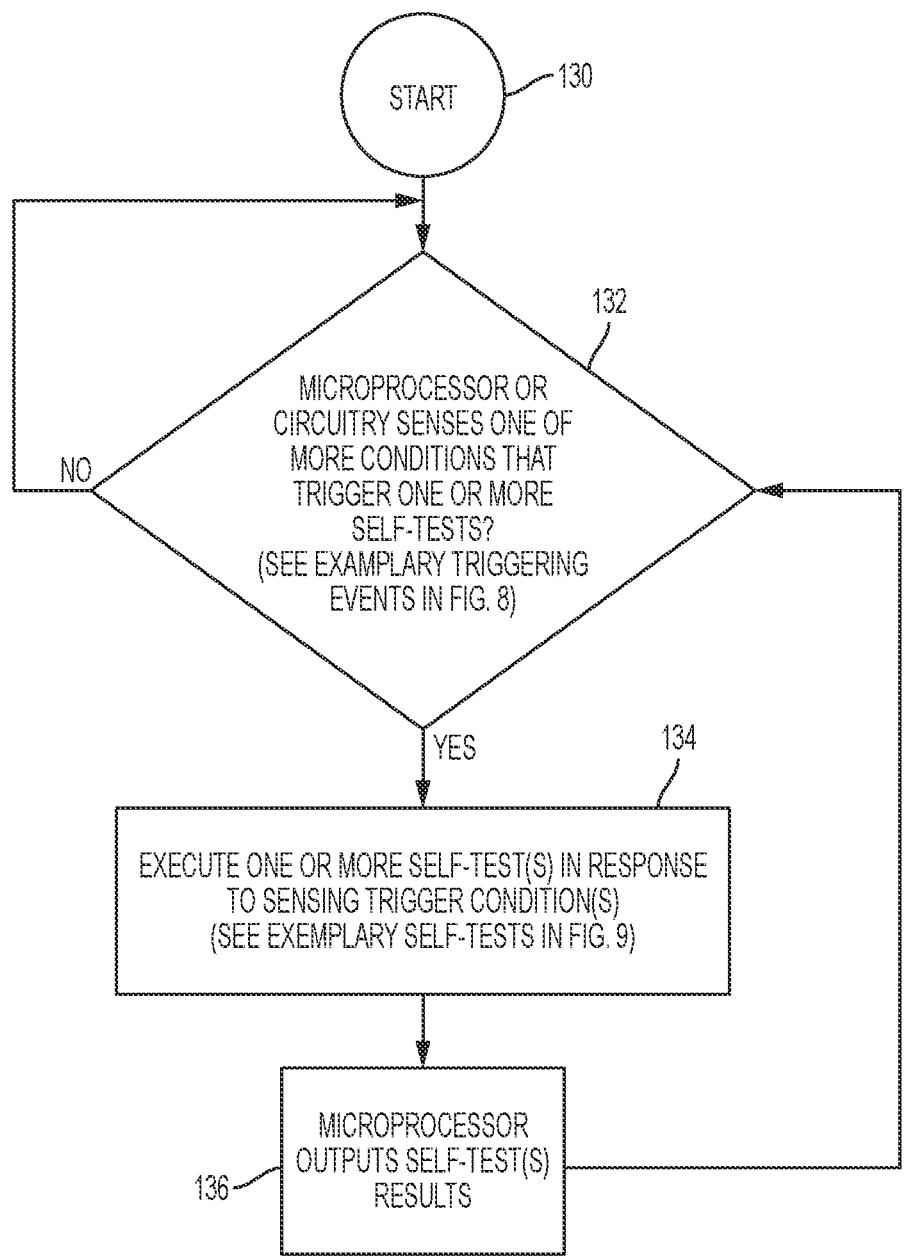
FIG. 7 is an example flow chart of a self-test process.

With reference to the generic flow diagram shown in FIG. 7, upon initialization, the microprocessor, under the control of a control program, advances from a start step 130 to a step 132 where the microprocessor senses for one or more conditions that trigger one or more self-tests. This sensing by the microprocessor can be on a periodic or aperiodic sampling basis of one or more inputs of the microprocessor or can be initiated by the microprocessor in response to a signal at one or more interruptible inputs of the microprocessor that are configured to respond to the signal by interrupting normal program execution and executing one or more interrupt service routines associated with said one or more inputs. The use of interruptible inputs and interrupt service routines to terminate normal program execution in a microprocessor is well known in the art and will not be discussed further herein for the purpose of simplicity.

In response to the microprocessor not sensing one or more trigger conditions, program flow loops on step 132. However, in response to the microprocessor sensing one or more trigger conditions, program flow advances from step 132 to step 134 wherein the microprocessor executes one or more self-tests in response to the sensed trigger conditions. Upon completion of the one or more self-tests, program flow advances to step 136 where the microprocessor outputs self-test results, e.g., on display screen 43. Program flow then returns to step 132.

A non-exhaustive list of example events that can trigger one or more self-tests in step 132 is shown in FIG. 8. A non-exhaustive list of example self-tests that the microprocessor can execute in step 134 in response to sensing a trigger condition is shown in FIG. 9.

Example Self-Test Process—Battery Replacement

Figure 10:
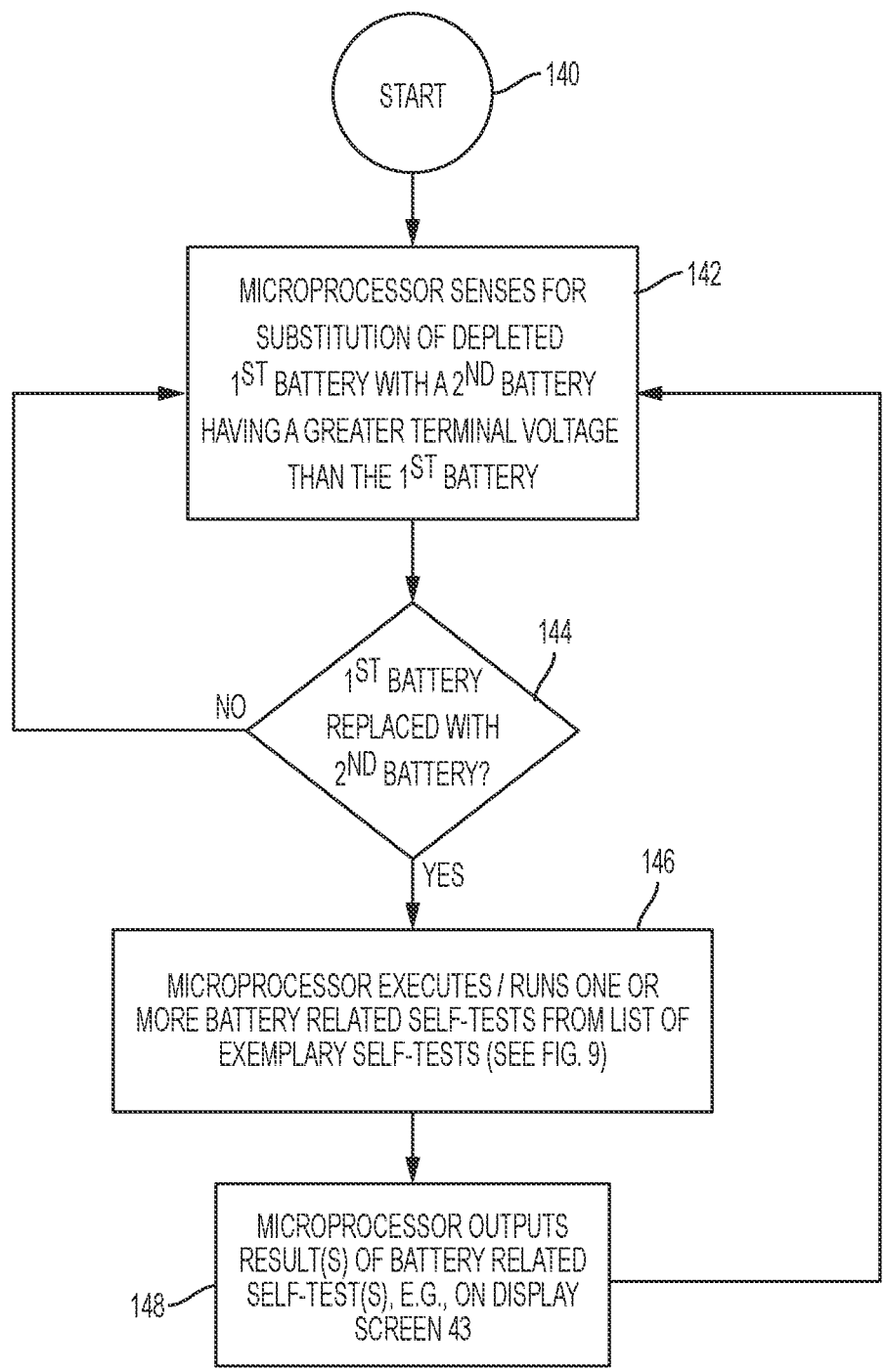
FIG. 10 is a flow chart of an example self-test process for a battery replacement.

With reference to FIG. 10, an example flow diagram of a self-test that can be run by the microprocessor in response to a depleted first battery being replaced with a second battery will now be described. After initialization, microprocessor advances from start step 140 to step 142 wherein the microprocessor senses for substitution of a depleted first battery with a second battery having a greater terminal voltage or charge than the first battery. This sensing by the microprocessor can occur via an A-to-D that is operative for sensing the terminal voltage of the first or second battery operatively coupled to the continuously on medical device, such as, without limitation, a continuous-use defibrillator.

If, in step 144, the microprocessor senses that the first battery has been replaced with the second battery having a greater terminal voltage or charge than the first battery, the microprocessor advances to step 146. In contrast, if, in step 144, the microprocessor does not sense the first battery has been replaced with the second battery having a greater terminal voltage or charge than the first battery, the microprocessor loops on steps 142 and 144 until sensing that the first battery has been replaced with the second battery having a greater terminal voltage or charge than the first battery.

Upon advancing to step 146, the microprocessor executes/runs one or more of the battery related self-tests from the list of example self-tests shown in FIG. 9. Upon completion of the one or more battery related self-tests in step 146, the microprocessor advances to step 148 where the microprocessor outputs the results of the one or more battery related self-tests, e.g., on display screen 43. Thereafter, program flow returns to step 142 where the microprocessor once again loops on steps 142-144 until sensing the substitution of a depleted first battery with a second battery having a greater terminal voltage or charge than the first battery.

Uses of Triggering Events and Example Self-Tests

In an example, the continuous-use medical device can be an ambulatory medical device, such as the wearable defibrillator 1 described above. However, this is not to be construed as limiting the invention since it is envisioned that a continuous-use medical device does not necessarily have to be an ambulatory medical device.

In an example, the continuous-use medical device, e.g., an ambulatory medical device, includes a sensing component to be disposed on a patient for detecting a physiological signal, e.g., a cardiac signal, of the patient. In an example, this sensing component can be one of the electrodes 7a-7d discussed above. Circuitry can be provided that comprises a monitoring component for monitoring for a triggering event and a self-test component for executing one or more self-test procedures on the ambulatory medical device. In one example, the monitoring component and self-test components can be controlled by circuitry 75 as described above and/or one or both processors 69, 71. For example, the monitoring component can include any suitable hardware and/or software module or element that can monitor for any one or combination of the example triggering events shown in FIG. 8, for example, and discussed above. Examples of monitoring components include an accelerometer, a piezoelectric device, or any other suitable and/or desirable device capable of detecting impact, especially impact above a certain level; a temperature sensor for sensing a temperature greater than or less than a predetermined maximum or minimum temperature; a moisture sensor for detecting moisture in excess of a predetermined moisture level; a strain sensor for detecting strain on a component, subsystem, or system of the medical device in excess of a predetermined strain level.

The monitoring component can also or alternatively include one or more elements for processing signals indicative of a triggering event. In an example, these elements can include a microprocessor, a programmable logic device (PLD), a programmable gate array (PGA), an application-specific integrated circuit (ASIC), analog and/or digital chips, one or more active components, such as transistors, passive components, or any combination of the foregoing.

The self-test component can include any one or combination of elements that are capable of performing operations associated with the one or more self-test procedures, including a microprocessor, computer memory or storage, a PLD, a PGA, an ASIC, analog and/or digital chips, active components, passive components, or any combination of the foregoing. Moreover, the monitoring component and the self-test component can be the same element or can include elements in common.

In an example, the monitoring component is always operational for monitoring during a period beginning from when the physiological signal of a patient is first sensed by the sensing component and ending when the monitoring is no longer needed for the patient. The medical device can also include a therapeutic element for delivering electrotherapy to a patient and can comprise a garment worn about a torso of the patient. When the continuous medical device comprises a garment worn about a torso of the patient, the period beginning when the physiological signal of the patient is first sensed can be when the garment is initially donned by the patient.

Examples of when the physiological signal of the patient can be first sensed include, without limitation, when the sensing component is in an operative position to commence acquiring the physiological signal of the patient, when the physiological signal is received from the sensing component by a processing component that is configured to process the physiological signal, when the physiological signal is processed by the processing component for the purpose treatment analysis, and/or when the physiological signal is stored in a memory.

Examples of when monitoring is no longer needed for the patient can include, without limitation, the patient being implanted with sensing and monitoring components; a changed physical condition of the patient whereupon the patient is medically required to use a different medical device; the patient being switched to a different device having more or fewer functions; the patient being switched to a different device used by a different caregiver; and/or the patient being moved from one environment to another (e.g., from department store to ambulance, from ambulance to hospital, from ambulance to helicopter, etc.).

In some implementations, the monitoring component can be operational for monitoring during at least one of the following events: changing of a power source of the ambulatory medical device; removal of and donning of the sensing component by patient for patient showering or bathing; replacement of a garment that comprises the ambulatory medical device worn about a torso of the patient; and replacement of a patient signal sensor. Replacement of the patient signal sensor can be in response to wear of the patient signal sensor over a time due to use.

In another example, the continuous medical device, such as, without limitation, an ambulatory medical device, can include a sensing component, such as one of the electrodes 7a-7d discussed above, to be disposed on a patient for detecting a physiological signal of the patient. The medical device can include circuitry configured to detect a change in a software or firmware configuration of the ambulatory medical device. This circuitry can include a microprocessor that is coupled to memory or storage that contains program code that is readable by the microprocessor and which enables the microprocessor to determine when a software or firmware configuration stored in another part of the same or a different memory or storage has changed.

In an example, the memory can store information regarding each software and/or firmware module stored on the ambulatory medical device. This information can include, without limitation, a checksum, a version number, and/or a revision number of each software and/or firmware module. Thereafter, operating under the control of the program code, the microprocessor can compare the checksum, version, and/or revision of one or more software or firmware modules stored on the ambulatory medical device with checksums, versions, and/or revisions stored in the memory for a match or mismatch. In the event of a mismatch, indicative of a change in a software or firmware configuration of the ambulatory medical device, a self-test component of the ambulatory medical device can execute one or more self-test procedures on the medical device. e.g., one or more of the self-tests shown in FIG. 9, for example.

The self-test component can include the same or a different microprocessor as was used to detect a change in the software or firmware configuration of the ambulatory device, either alone or in combination with other components required to perform the one or more of the self-tests. In an example, the self-test component can perform a system-wide test (test no. 11 in FIG. 9) that not only tests one or more components but also tests, indirectly, the operational capabilities of intermediate components, such as an analog-to-digital converter, gate arrays, multiplexors, and biasing elements.

In an example, the change in the software configuration can comprise a software or firmware update to software or firmware of the ambulatory medical device. In another example, the change in the software or firmware configuration can comprise an update to one or more device parameters set in the ambulatory medical device. An example of a device parameter includes a threshold level. Examples of threshold levels include a maximum moisture threshold to be detected before triggering a self-test, a maximum threshold temperature, above which a self-test is triggered, or a minimum temperature to be sensed before triggering a self-test.

Another example continuous-use medical device, such as an ambulatory medical device, includes a sensing component, such as, without limitation, one of the electrodes, 7a-7d discussed above, to be disposed on a patient for detecting a physiological signal of the patient. Circuitry is provided comprising a monitoring component for monitoring a triggering event and a self-test component for executing one or more self-test procedures on the ambulatory medical device. The monitoring component and the self-test component can be as described above.

In this example, the monitoring component is always operational for monitoring whether or not a primary source of power is available in the ambulatory medical device.

In an example of such an ambulatory medical device, the circuitry can include first and second components that are coupled to the primary source of power. A secondary source of power can be coupled to the first component, but not to the second component, for supplying electrical power to the first component when the primary source of power is not supplying electrical power to the first component, such as when the primary source of power is either unable to supply electrical power or is unavailable to supply electrical power. Examples of when the primary source of power is either unable to or unavailable to supply electrical power, whereupon the secondary source of power supplies power to the first component, includes (1) when the primary source of power is a replaceable battery that is in the process of being replaced: and (2) when the primary source of power to the first and second components has been terminated by an action by the patient, e.g., when the garment is removed from the patient, or when power from the primary source of power is terminated to the first and second components for some purpose, such as the patient removing the garment, including the primary source of power, for showering or bathing, or the removal of one or more of the electrode assembly, monitor 5, distribution node 11, electrodes 7a-7d, and/or therapy electrodes 13a-13c from one garment and installing these elements in another garment.

In an example, the primary source of power can be a main battery that is used with the ambulatory medical device and the secondary source of power can be a secondary or backup battery, a capacitor, or a supercapacitor, such as a double layer capacitor or a lithium-ion capacitor, an inductor, or any other energy storage device that can supply electrical power only to a subset of the components of the ambulatory medical device when the primary source of power is unavailable or not able to supply electrical power.

In an example, the secondary source of power supplies power to the first component, but not to the second component, when the primary source of power is unable to or unavailable to supply electrical power. In an example, the first component can be the monitoring component for monitoring for a triggering event. In another example, the first component can be the combination of the monitoring component and the self-test component for executing one or more self-test procedures on the ambulatory medical device.

In an example, in response to the monitoring component detecting an event when the primary source of power is not able to or is not available to supply electrical power to the first component, the first component, operating with electrical power from the secondary source of power, can (a) cause a first subset of the one or more self-test procedures to be performed on the ambulatory medical device or (b) delay performing a second subset of the one or mom self-test procedures until the primary source of power is supplying electrical power to the first component. In an example, this delay can be almost zero, such as when the primary source of power has been momentarily disconnected.

The first and second subsets of the one or more self-test procedures can be the same or different.

In an example, a plurality of self-test procedures can be provided for execution on the ambulatory medical device. Within a first period of time following the primary source of power becoming not able to or not available to supply electrical power to the first component, the plurality of self-test procedures can be performed. Following this first period of time, less than all of the plurality of self-test procedures can be performed.

In an example, the secondary source of power and the first component can be configured such that step (a) or step (b) above can be performed for a period of time when the primary source of power is not able to or is not available to supply electrical power to the first component that is at least one week or at least one month.

In an example, the first component can be operative for directly or indirectly monitoring for the occurrence of the event. The first component can indirectly monitor for the occurrence of the event via a component, subsystem, or system of the ambulatory medical device that is configured to convert the event into form for processing by the first component. In an example, the first component can comprise one or more microprocessors, microcontrollers, or other integrated device such as, without limitation, one or more ASICs. PLDs, and/or FPGAs. In an example, the first component is a low power consumption device that is configured in the continuous-use medical device to always be powered on, either from the primary source of power or the secondary source of power—in an example, when the primary source of power is not supplying power to the first component, to detect for one or more triggering events and to execute one or more self-tests (or cause one or more self-tests to be executed) in response to detecting the one or mom triggering events.

Another example continuous-use medical device, such as an ambulatory medical device, includes a sensing component, such as one of the electrodes 7a-7d, to be disposed on a patient for detecting a physiological signal of the patient. The ambulatory medical device comprises a monitoring component for monitoring for a triggering event and a self-test component for executing one or more self-test procedures on the ambulatory medical device. The monitoring component and/or the self-test component can be the same as described above.

The monitoring component can be always operational (powered on) for monitoring during a monitoring period beginning from when the sensing component is first configured to begin detection of the physiological signal of the patient and ending when the sensing component is configured to no longer be capable of detecting the physiological signal of the patient. An example of when the sensing component is first configured to begin the detection of the physiological signal of the patient occurs when a component, subsystem, or system of the ambulatory medical device is activated whereupon it becomes capable of receiving data from the monitoring component indicative of the detected physiological signal of the patient. An example of when this sensing component is configured to no longer be capable of detecting the physiological signal of the patient occurs when power is removed from said component subsystem or system of the ambulatory medical device.

The ambulatory medical device can further include a therapeutic element for delivering electrotherapy to the patient. The continuous-use medical device can also include a garment worn about a torso of the patient.

In another example, a self-test circuit of the ambulatory medical device still receives power even when the primary source of power is not supplying power to the ambulatory medical device, such as when the ambulatory medical device is shut off for (1) replacement of the primary source of power, e.g., a main battery of the ambulatory medical device, (2) the patient shuts down the ambulatory medical device for showering or bathing, and/or (3) exchanging one garment of the ambulatory medical device for another garment. In any of these instances, when the device is shut off, the self-test circuit is still capable of performing one or more self-test procedures, such as, without limitation, detecting a moisture level via the moisture detector, detecting a temperature via the temperature sensor, or any one or more of the self-tests disclosed in FIG. 9. In an example, the monitoring component and/or the self-test circuit can be one or more low power consumption devices that are configured to always be powered on for detecting for one or more triggering events and/or for executing one or more self-tests (or causing one or more self-tests to be executed) in response to detecting the one or more triggering events, respectively.

Another example continuous-use medical device, such as an ambulatory medical device, includes a monitoring component for monitoring for one or more triggering events different from an intended medical use of or intended medical purpose for the medical device that could potentially prevent the medical device from functioning for its intended purpose; and a self-test component responsive to the one or more triggering events for executing one or more self-tests procedures on the ambulatory medical device.

The one or more triggering events can include: excessive mechanical shock; exposure to temperature greater than a predetermined maximum temperature or less than a predetermined minimum temperature; exposure to excessive moisture; excessive strain on a component, subsystem, or system of the medical device: exposure to a temperature change outside of predetermined limits; exposure to a rate of temperature change outside of predetermined limits; prolonged vibration outside a time limit or an amplitude limit; passage of time beyond a predetermined limit; and/or a change in ambient pressure beyond a predetermined limit.

In an example, the continuous-use medical device can include a ambient pressure sensor that is operative for sensing ambient pressure and providing an indication thereof to the monitoring component which can be configured to compare the indication of the sensed ambient pressure to a predetermined pressure value. Detection that the indication of the sensed ambient pressure is greater than (or less than) the predetermined pressure value can be treated by monitoring component as a triggering event that the self-test component can be responsive to for executing one or more self-tests procedures on the ambulatory medical device.

The embodiments have been described with reference to various examples. Modifications and alterations will occur to others upon reading and understanding the foregoing examples. Accordingly, the foregoing examples am not to be construed as limiting the disclosure.

What is claimed is:

1. An ambulatory medical device with self-testing capability, the ambulatory medical device comprising:
a plurality of sensing electrodes configured to detect electrocardiogram signals of a patient;
a plurality of therapy pads configured to deliver one or more treatment shocks to the patient;
a garment configured to be worn by the patient, the garment configured to support the plurality of sensing electrodes and the plurality of therapy pads, such that the plurality of sensing electrodes and the plurality of therapy pads are positioned against the patient when the patient wears the garment;
at least one processor coupled to the plurality of sensing electrodes and the plurality of therapy pads, the at least one processor configured to:
monitor operation of the ambulatory medical device during a device monitoring period during which the ambulatory medical device is continuously operational,
analyze the electrocardiogram signals of the patient during the device monitoring period for one or more treatable cardiac arrhythmia conditions in the patient, wherein the one or more treatable cardiac arrhythmia conditions are treated by one or more of pacing, cardioversion, and/or defibrillation pulses delivered as the one or more treatment shocks to the patient,
detect a self-test triggering event during the device monitoring period based on at least one of an impact event or a vibration event experienced by the ambulatory medical device, and
in response to detecting the self-test triggering event based on the at least one of the impact event or the vibration event, initiate a self-test of the ambulatory medical device.

2. The ambulatory medical device of claim 1, wherein the device monitoring period begins when the plurality of sensing electrodes detects the electrocardiogram signals of the patient.

3. The ambulatory medical device of claim 2, wherein the device monitoring period ends when the plurality of sensing electrodes no longer detects the electrocardiogram signals of the patient.

4. The ambulatory medical device of claim 1, further comprising at least one of an impact detecting device or a vibration detecting device.

5. The ambulatory medical device of claim 4, wherein:
the impact detecting device or the vibration detecting device comprises one or more of an accelerometer, a piezoelectric device, an electromechanical switch, or a mechanical switch; and
the self-test triggering event is detected using at least one of the impact detecting device or the vibration detecting device.

6. The ambulatory medical device of claim 1, further comprising a memory, wherein the at least one processor is further configured to store, in the memory, a set of results of the self-test.

7. The ambulatory medical device of claim 6, further comprising a network interface, wherein the at least one processor is further configured to transmit, via the network interface, the set of results of the self-test.

8. The ambulatory medical device of claim 1, further comprising a memory, wherein the at least one processor is further configured to, in response to detecting the self-test triggering event, store, in the memory, a flag.

9. The ambulatory medical device of claim 8, wherein the flag, when retrieved from the memory, provides an indication that the at least one of the impact event or the vibration event occurred.

10. The ambulatory medical device of claim 1, wherein the at least one of the impact event or the vibration event is based on identifying at least one of (a) an impact duration that exceeds a predetermined impact duration or (b) a vibration duration that exceeds a predetermined vibration duration.

11. The ambulatory medical device of claim 10, wherein the at least one of the impact event or the vibration event comprises an event that affects safety of the patient during operation of the ambulatory medical device.

12. The ambulatory medical device of claim 10, wherein the self-test of the ambulatory medical device comprises a self-test of one or more devices, components, or subsystems of the ambulatory medical device to ensure that neither the impact event nor the vibration event has adversely affected safety of the patient during operation of the ambulatory medical device.

13. A method for self-testing an ambulatory medical device, the method comprising:
monitor operation of an ambulatory medical device worn by a patient during a device monitoring period during which the ambulatory medical device is continuously operational;
receive electrocardiogram signals of the patient from sensing circuitry that forms part of the ambulatory medical device;
analyze the electrocardiogram signals of the patient during the device monitoring period for one or more treatable cardiac arrhythmia conditions in the patient, wherein the one or more treatable cardiac arrhythmia conditions are treated by one or more of pacing, cardioversion, and/or defibrillation pulses delivered as one or more treatment shocks to the patient;
detect a self-test triggering event during the device monitoring period based on at least one of an impact event or a vibration event experienced by the ambulatory medical device; and
in response to detecting the self-test triggering event based on the at least one of the impact event or the vibration event, initiate a self-test of the ambulatory medical device.

14. The method of claim 13, wherein the self-test triggering event is detected using at least one of an impact detecting device or a vibration detecting device.

15. The method of claim 14, wherein the impact detecting device or the vibration detecting device comprises one or more of an accelerometer, a piezoelectric device, an electromechanical switch, or a mechanical switch.

16. The method of claim 13, further comprising storing, in a memory, a set of results of the self-test.

17. The method of claim 16, further comprising transmitting, via a network interface, to a remote server, the set of results of the self-test.

18. The method of claim 16, further comprising, in response to detecting the self-test triggering event, storing, in the memory, a flag that provides an indication that the at least one of the impact event or the vibration event occurred.

19. The method of claim 13, wherein the at least one of the impact event or the vibration event is based on identifying at least one of (a) an impact level that exceeds a predetermined impact level or (b) a vibration level that exceeds a predetermined vibration level.

20. The method of claim 19, wherein the at least one of the impact event or the vibration event comprises an event that affects safety of the patient during operation of the ambulatory medical device.

21. The method of claim 19, wherein the self-test of the ambulatory medical device comprises a self-test of one or more devices, components, or subsystems of the ambulatory medical device to ensure that neither the impact event nor the vibration event has adversely affected patient safety during operation of the ambulatory medical device.

* * * * *